US007750204B2

(12) United States Patent
Kodama et al.

(10) Patent No.: US 7,750,204 B2
(45) Date of Patent: Jul. 6, 2010

(54) METHODS FOR PRODUCING ANTIBODY

(75) Inventors: Tatsuhiko Kodama, Tokyo (JP); Kou-Ichi Jishage, Shizuoka (JP); Nobuo Kamada, Shizuoka (JP); Yoshiki Yamada, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/516,603

(22) PCT Filed: Jun. 4, 2003

(86) PCT No.: PCT/JP03/07071

§ 371 (c)(1),
(2), (4) Date: Jun. 8, 2005

(87) PCT Pub. No.: WO03/104453

PCT Pub. Date: Dec. 18, 2003

(65) Prior Publication Data

US 2005/0222391 A1    Oct. 6, 2005

(30) Foreign Application Priority Data

Jun. 5, 2002   (JP)   ............................. 2002-164834
Jun. 20, 2002  (JP)   ............................. 2002-180351

(51) Int. Cl.
*C12P 21/00* (2006.01)
(52) U.S. Cl. .................................. 800/6; 800/3; 800/18
(58) Field of Classification Search ...................... 800/3, 800/8, 21
See application file for complete search history.

(56) References Cited

U.S. PATENT DOCUMENTS

| 5,500,346 | A  | 3/1996  | Bright et al. |
| 5,849,525 | A  | 12/1998 | Hediger |
| 6,270,978 | B1 | 8/2001  | Bright et al. |
| 6,713,278 | B1 | 3/2004  | Bouvier et al. |
| 2005/0004227 | A1 | 1/2005  | Saitoh |
| 2005/0222391 | A1 | 10/2005 | Kodama et al. |
| 2005/0281825 | A1 | 12/2005 | Kodama et al. |
| 2006/0084119 | A1 | 4/2006  | Saitoh et al. |
| 2006/0210569 | A1 | 9/2006  | Kodama et al. |
| 2008/0040820 | A1 | 2/2008  | Kodama et al. |

FOREIGN PATENT DOCUMENTS

| EP | 1142473    | 10/2001 |
| EP | 1 731 032  | 12/2006 |
| JP | 6-261761   | 9/1994 |
| JP | 8-134100   | 5/1996 |
| JP | 11-000172  | 1/1999 |
| JP | 2001-139496 | 5/2001 |
| JP | 2001-197846 | 7/2001 |
| WO | WO 97/19919 | 6/1997 |
| WO | WO 98/46777 | 10/1998 |
| WO | WO 00/28016 | 5/2000 |
| WO | WO 03/033024 | 4/2003 |
| WO | WO 03/047621 | 6/2003 |
| WO | WO 03/083116 | 10/2003 |
| WO | WO 03/104453 | 12/2003 |

OTHER PUBLICATIONS

Satoi et al., J. Virol., 2001, vol. 75, No. 24, pp. 12121-12127.*
Leiter et al. (2002) Diabetologia 45:296-308.*
Lariviere et al. (2001) J. Pharm. And Exp. Therap. 297:467:473.*
Mancini et al. (1993) J. Med. Virol 39 : 67-74.*
Tsuchiya M. (1.21.2003) Therapeutic Antibody Presentation, pp. 1-21.*
Houdebine et al. (2000) Transgenic Research 9:305-320.*
Kolb et al. (1999) Gene 227:21-31.*
Murray (1999) Theriogenology 51:149-159.*
Sigmund, C., (2000) Arterioscler. Thromb. Vasc. Biol., p. 1425-1429.*
Lindley et al., "Production of monoclonal antibodies using recombinant baculovirus displaying gp64-fusion proteins," *J. Immunol. Methods.*, 234:123-35 (2000).
Basu et al., "Development and Utility of Anti-PepT1 Anti-Peptide Polyclonal Antibodies," *Pharmaceutical Research*, 15:338-342 (1998).
Basu et al., "Screening of Anti-PepT1 Antibodies Using Indirect ELISA," *Pharmaceutical Research*, 13(9 Suppl.):S-37, Abstract No. APQ 1137 (1996).
Blissard et al., "Location, Sequence, Transcriptional Mapping, and Temporal Expression of the gp64 Envelope Glycoprotein Gene of the *Orgyia pseudotsugata* Multicapsid Nuclear Polyhedrosis Virus," *Virology*, 170:537-555 (1989).
Friedman et al., "Characterization of the Intestinal Transport Parameters for Small Peptide Drugs," *J. Control. Release*, 13:141-146 (1990).
Friedman et al., "Passive and Carrier-Mediated Intestinal Absorption Components of Two Angiotensin Converting Enzyme (ACE) Inhibitor Prodrugs in Rats: Enalapril and Fosinopril," *Pharm. Res.*, 6:1043-1047 (1989).
Ganapathy et al., "Proton-coupled solute transport in the animal cell plasma membrane," *Curr. Opin. Cell Biol.*, 3:695-701 (1991).
Gonzalez et al., "An Oligopeptide Transporter Is Expressed at High Levels in the Pancreatic Carcinoma Cell Lines AsPc-1 and Capan-2," *Cancer Res.*, 58:519-525 (1998).
Higgins, "ABC Transporters: From Microorganisms to Man," *Annu. Rev. Cell Biol.*, 8:67-113 (1992).
Knütter et al., "A Novel Inhibitor of the Mammalian Peptide Transporter PEPT1," *Biochemistry*, 40:4454-4458 (2001).

(Continued)

*Primary Examiner*—Peter Paras, Jr.
*Assistant Examiner*—Marcia S. Noble
(74) *Attorney, Agent, or Firm*—Fish & Richardson P.C.

(57) ABSTRACT

This invention provides methods for producing antibodies, wherein the methods comprise the step of administering an immunogen comprising both a target antigen and a background antigen to transgenic animals, into which a gene coding for the background antigen has been introduced. Since immunotolerance to the background antigens have thus been induced in the transgenic animals, the animals efficiently produce antibodies to target antigens.

2 Claims, 9 Drawing Sheets

OTHER PUBLICATIONS

Lee et al., "Biopharmaceutics of transmucosal peptide and protein drug administration: role of transport mechanisms with a focus on the involvement of PepT1," *J. Control. Release*, 62:129-140 (1999).

Liang et al., "Human Intestinal H+/Peptide Cotransporter. Cloning, Functional Expression, and Chromosomal Localization," *J. Biol. Chem.*, 270:6456-6463 (1995).

Liu et al., "Molecular cloning of PEPT2, a new member of the H+/peptide cotransporter family, from human kidney," *Biochim. Biophys. Acta*, 1235:461-466 (1995).

Loisel et al., "Recovery of homogeneous and functional $\beta_2$-adrenergic receptors from extracellular baculovirus particles," *Nat. Biotechnol.*, 15:1300-1304 (1997).

Mangor et al., "A GP64-Null Baculovirus Pseudotyped with Vesicular Stomatitis Virus G Protein," *J. Virol.*, 75:2544-2556 (2001).

Mikhailov et al., "Expression of functionally active ATP-sensitive K-channels in insect cells using baculovirus," *FEBS Lett.*, 429:390-394 (1998).

Mrsny, "Oligopeptide Transporters as Putative Therapeutic Targets for Cancer Cells," *Pharm. Res.*, 15:816-818 (1998).

Muranushi et al., "Transport Characteristics of Ceftibuten, a New Oral Cephem, in Rat Intestinal Brush-Border Membrane Vesicles: Relationship to Oligopeptide and Amino β-Lactam Transport," *Pharm. Res.*, 6:308-312 (1989).

Nakanishi et al., "Cancer Cell-Targeted Drug Delivery Utilizing Oligopeptide Transport Activity," *Int. J. Cancer*, 88:274-280 (2000).

Nakashima et al., "Kinetics and Mechanism of In Vitro Uptake of Amino-β-Lactam Antibiotics by Rat Small Intestine and Relation to the Intact-Peptide Transport System," *Biochem. Pharmacol.*, 33:3345-3352 (1984).

Noe et al., "Characterization of the Mouse Bile Salt Export Pump Overexpressed in the Baculovirus System," *Hepatology*, 33:1223-1231 (2001).

Ogihara et al., "Immuno-Localization of H+/Peptide Cotransporter in Rat Digestive Tract," *Biochem. Biophys. Res. Commun.*, 220:848-852 (1996).

Okano et al., "H+ Coupled Uphill Transport of Aminocephalosporins via the Dipeptide Transport System in Rabbit Intestinal Brush-border Membranes," *J. Biol. Chem.*, 261:14130-14134 (1986).

Sai et al., "Immunolocalization and pharmacological relevance of oligopeptide transport PepT1 in intestinal absorption of β-lactam antibiotics," *FEBS Lett.*, 392:25-29 (1996).

Sai et al., "Selective Delivery of Peptide Anticancer Drugs via Oligopeptide Transporter Expressed in Cancer Cells," *Proceedings of the Millennium World Congress of Pharmaceutical Science*, p. 61, Abstract No. 2-2124 (Apr. 16-20, 2000).

Saito et al., "Cloning and Chracterization af a Rat H+/Peptide Cotransporter Mediating Absorption of β-Lactam Antibiotics in the Intestine and Kidney," *J. Pharmacol. Exp. Ther.*, 275:1631-1637 (1995).

Saito et al., "Molecular cloning and tissue distribution of rat peptide transporter PEPT2," *Biochim. Biophys. Acta*, 1280:173-177 (1996).

Sakaguchi et al., "The Iron Channel Activity of the Influenza Virus $M_2$ Protein Affects Transport through the Golgi Apparatus," *J. Cell. Biol.*, 133:733-747 (1996).

Satoi et al., "Genetic Immunization of Wild-Type and Hepatitis C Virus Transgenic Mice Reveals a Hierarchy of Cellular Immune Response and Tolerance Induction against Hepatitis C Virus Structural Proteins," *J. Virol.*, 75:12121-12127 (2001).

Shen et al., "Localization of PEPT1 and PEPT2 proton-coupled oligopeptide transporter mRNA and protein in rat kidney," *Am. J. Physiol.*, 276:F658-F665 (1999).

Steiner et al., "The PTR family: a new group of peptide transporters," *Mol. Microbiol.*, 16:825-834 (1995).

Strehlow et al., "Retroviral membrane display of apoptotic effector molecules," *Proc. Natl. Acad. Sci. USA*, 97:4209-4214 (2000).

Sugano et al., "Quantitative Structure-Intestinal Permeability Relationship of Benzamidine Analogue Thrombin Inhibitor," *Bioorg. Med. Chem. Lett.*, 10:1939-1942 (2000).

Sun et al., "Drug Inhibition of Gly-Sar Uptake and hPepT1 Localization using hPepT1-GFP Fusion Protein," *AAPS Pharmsci.*, 3(1):article 2, pp. 1-9 (2001).

Szakács et al., "Characterization of the ATPase Cycle of Human ABCA1: Implications for Its Function as a Regulator Rather Than an Active Transporter," *Biochem. Biophys. Res. Commun.*, 288:1258-1264 (2001).

Takahashi et al., "Interaction of β-Lactam Antibiotics with H+.Peptide Cotransporters in Rat Renal Brush-Border Membranes," *J. Pharmacol. Exp. Ther.*, 286:1037-1042 (1998).

Terada et al., "Characterization of Stably Transfected Kidney Epithelial Cell Line Expressing Rat H+/Peptide Contransporter PEPT1: Localization of PEPT1 and Transport of β-Lactam Antibiotics," *J. Pharmacol. Exp. Ther.*, 281:1415-1421 (1997).

Terada et al., "Peptide Transporter Family," *Tanpakushitsu Kakusan Koso* (*Protein, Nucleic Acid and Enzyme*), 46:621-628 (2001) (Concise explanation in English enclosed).

Zhou et al., "Characterization of an oligopeptide transporter in renal lysosomes," *Biochim. Biophys. Acta*, 1466:372-378 (2000).

Blissard et al., "Baculovirus gp64 Gene Expression: Analysis of Sequences Modulating Early Transcription and Transactivation by IE1," *J. Virol.*, 65:5820-5827 (1991).

Hsu et al., "Overexpression of Human Intestinal Oligopeptide Transporter in Mammalian Cells via Adenoviral Transduction," *Pharm. Res.*, 15:1376-1381 (1998).

Karaki et al., "Production of anti-HLA class I alloantibodies using HLA-B51 transgenic mice," *Nihonmenekigakkaisoukai Gakujutsushuukaikiroku*, Abstract No. C61, p. 197 (1990) (English translation included).

Nishimura et al., "Expression of the Human MHC, HLA-DQw6 Genes Alters the Immune Response in C57BL/6 Mice," *J. Immunol.*, 145:353-360 (1990).

Okamoto et al., "Generation of monoclonal antibodies directed against allotypic epitopes of HLA class II antigen by utilizing HLA-DQw6 transgenic mice," *Nihonmenekigakkaisoukai Gakujutsushuukaikiroku*, Abstract No. C62, p. 197 (1990) (English translation included).

Tamura et al., "CD14 Transgenic Mice Expressing Membrane and Soluble Forms: Comparisons of Levels of Cytokines and Lethalities in Response to Lipopolysaccharide Between Transgenic and Non-Transgenic Mice," *International Immunology*, 11:333-339 (1999).

Watanabe et al., "Enhanced Immune Responses in Transgenic Mice Expressing a Truncated Form of the Lymphocyte Semaphorin CD100," *J. Immunol.* 167: 4321-4328 (2001).

ATCC Web Catalog, "Tumor Cell Lines" www.atcc.org (2007) 15 pages.

Cancer Classification, WHO, http://training.seer.cancer.gov/module_. . . ase/unit3_categories2_by_histology.html (2005) 3 pages.

Grever et al., "The National Cancer Institute: Cancer Drug Discovery and Development Program," *Seminars in Oncology*, 19(6): 622-638 (1992).

Braunagel et al., "Autographa californica Nuclear Polyhedrosis Virus, PDV, and ECV Viral Envelopes and Nucleocapsids: Structural Proteins, Antigens, Lipid and Fatty Acid Profiles," *Virology*, 202:315-320 (1994).

Grabherr et al., "Developments in the use of baculoviruses for the surface display of complex eukaryotic proteins," *Trends in Biotechnology*, 19:231-236 (2001).

Marheineke et al., "Lipid composition of Spodoptera frugiperda (Sf9) and Trichoplusia ni (Tn) insect cells used for baculovirus infection," *FEBS Letters*, 441:49-52 (1998).

Campbell, "Monoclonal antibody technology", Elsevier Science Publishing Company Inc., pp. 1-33.(1984).

D'Onofrio, "Making the case for cancer prevention in the schools", *Journal of School Health*, 225-231 (1989).

Inoue et al., "Regulation of human peptide transporter 1 (PEPT1) in gastric cancer cells by anticancer drugs", *Cancer Letters*, 230:72-80 (2005).

Pardee, "Tumor progression—targets for differential therapy", *Journal of Cellular Physiology*, 209:589-591 (2006).

Winter et al., "Man-made antibodies", *Nature*, 349:293-299 (1991).

Boublik et al., "Eukaryotic Virus Display: Engineering the major Surface Glycoprotein of the Autographa californica Nuclear Polyhedrosis Virus (ScNPV) for the Presentation of Foreign Proteins on the Virus Surface," *Biotechnology*, 13 1079-1084 (1995).

Garcia et al., "cDNA Cloning of MCT2, A Second Monocarboxylate Transporter Expressed in Different Cells than MCT1," The Journal of Biological Chemistry, 270: 1843-1849 (1995).
Gonzalez et al., "An Oligopeptide Transporter is Expressed at High Levels in the Pancreatic Carcinoma Cell Lines AsPc-1 and Capan-2," Cancer Res., 58(3): 519-525 (1998).
Hefferon et al., "Host Cell receptor Binding by Baculovirus GP64 and Kinetics of Virion Entry," Virology, 258: 455-468 (1999).
Kamada et al., "Generation of GP64-Expressing Mice and Induction of Tolerance to Budding Baculoviruses," Nihon Bunshi Seibutsu Gakkai Nenkai Program Koen Yoshishu, Abstract No. IPC-162, p. 659 (2003) (Translation Provided).
Lu et al., "Characterization of a Truncated Soluble Form of the Baculovirus (AcMNPV) Major Envelope Protein Gp64," Protein Expression and Purification, 24: 196-201 (2002).
Miyasaka et al., "Characterization of Human Taurine Transported Expressed in Insect Cells Using a Recombinant Baculovirus," Protein Expression and Purification, 23: 389-397 (2001).
Monsma et al., "Identification of a Membrane Fusion Domain and an Oligomerization Domain in the Baculovirus GP64 Envelope Fusion Protein," Journal of Virology, 69: 2583-2595 (1995).
Monsma et al., "The GP64 Envelope Fusion Protein is an Essential Baculovirus Protein Required for Cell-to-Cell Transmission of Infection," Journal of Virology, 70: 4607-4616 (1996).
Ohtomo et al., "Generation of Functional Antibodies Using GP64-Expressing/CCR2 Knock-Out Mice and CCR2-Expressing Baculoviruses," Nihon Bunshi Seibutsu Gakkai Nenkai Program Koen Yoshishu, Abstract No. 1PC-164, 26: 660 (2003) (Translation Provided).
Seliger et al., "Analysis of the MHC Class I Antigen Presentation Machinery in Human Embryonal CarcinomasL Evidence for Deficiencies in TAP, LMC, and MHC Class I Expression and Their Upregulation by IFN-γ," Scandinavian Journal of Immunology, 46: 625-632 (1997) (Abstract).
Suzuki et al., "Effects of Retinoic Acid on Lung Smooth Muscle Cells," FASEB Journal, 18: 355-356 (2004) (Abstract).
Fish & Richardson P.C., Response to Restriction Requirement dated Jun. 6, 2007 in U.S. Appl. No. 10/492,376, filed Jul. 6, 2007, 1 page.
Fish & Richardson P.C., Amendment in Reply to Action dated Sep. 17, 2007 in U.S. Appl. No. 10/492,376, filed Jan. 17, 2008, 10 pages.
Japanese Patent Office, International Preliminary Report on Patentability for App. Ser. No. PCT/JP02/10743, dated Apr. 21, 2003, 4 pages.
Japanese Patent Office, International Search Report for App. Ser. No. PCT/JP02/10743, mailed Feb. 4, 2003, 2 pages.
Fish & Richardson P.C., Response to Restriction Requirement dated Jun. 13, 2008 in U.S. Appl. No. 10/497,900, filed Jul. 11, 2008, 1 page.
Fish & Richardson P.C., Amendment in Reply to Action dated Sep. 19, 2007 in U.S. Appl. No. 10/497,900, filed Feb. 19, 2008, 9 pages.
Fish & Richardson P.C., Amendment in Reply to Action dated Oct. 30, 2008 in U.S. Appl. No. 10/497,900, filed Mar. 27, 2009, 8 pages.
Japanese Patent Office, International Preliminary Report on Patentability for App. Ser. No. PCT JP02/12708, dated Aug. 12, 2003, 6 pages.
Japanese Patent Office, International Search Report for App. Ser. No. PCT/JP02/12708, mailed Mar. 11, 2003, 4 pages.
Fish & Richardson P.C., Response to Restriction Requirement dated Jan. 25, 2007 in U.S. Appl. No. 10/509,343, filed Feb. 26, 2007, 6 pages.
Fish & Richardson P.C. Amendment in Reply to Action dated May 16, 2007 in U.S. Appl. No. 10/509,343, filed Nov. 16, 2007, 24 pages.
USPTO Interview Summary in U.S. Appl. No. 10/509,343, dated Mar. 6, 2008, 4 pages.
Fish & Richardson P.C. Amendment in Reply to Action dated Feb. 5, 2008 in U.S. Appl. No. 10/509,343, filed Mar. 5, 2009, 10 pages.
USPTO Notice of Allowance in U.S. Appl. No. 10/509,343, dated May 27, 2009, 17 pages.
Japanese Patent Office, International Preliminary Report on Patentability for App. Ser. No. PCT/JP03/03975, dated Sep. 8, 2003, 6 pages.
Japanese Patent Office, International Search Report for App. Ser. No. PCT/JP03/03975, mailed May 6, 2003, 2 pages.

Fish & Richardson P.C., Amendment in Reply to Action dated Oct. 5, 2007 in U.S. Appl. No. 10/550,987, filed Mar. 5, 2008, 9 pages.
Fish & Richardson P.C., Amendment in Reply to Action dated Jun. 13, 2008 in U.S. Appl. No. 10/550,987, filed Feb. 19, 2009, 12 pages.
USPTO Office Action in U.S. Appl. No. 10/550,987, dated Mar. 31, 2009, 12 pages.
European Search Report for App. Ser. No. EP 04723785.4, dated Jul. 12, 2006, 2 pages.
Japanese Patent Office, International Preliminary Report on Patentability for App. Ser. No. PCT/JP04/004331, dated Dec. 17, 2004, 5 pages.
Japanese Patent Office, International Search Report for App. Ser. No. PCT/JP04/004331, mailed Jun. 22, 2004, 2 pages.
Fish & Richardson P.C., Amendment in Reply to Action dated Oct. 16, 2008 in U.S. Appl. No. 10/594,690, filed Apr. 16, 2009, 9 pages.
USPTO Final Office Action in U.S. Appl. No. 10/594,690, mailed Jun. 8, 2009, 11 pages.
Japanese Patent Office, International Preliminary Report on Patentability for App. Ser. No. PCT/JP2005/006298, dated Feb. 8, 2006, 10 pages.
Japanese Patent Office, International Search Report for App. Ser. No. PCT/JP2005/006298, mailed Jul. 12, 2005, 3 pages.
Japanese Patent Office, International Preliminary Report on Patentability for App. Ser. No. PCT/JP03/07071, dated Nov. 21, 2003, 7 pages.
Japanese Patent Office, International Search Report for App. Ser. No. PCT/JP03/07071, mailed Jul. 22, 2003, 3 pages.
Bachmann et al., "Correlation of Tolerogenicity of a Viral Antigen with Its Immunogenicity," The Journal of Immunology, 158:5106-5111 (1997).
Ramamoorthy et al., "Proton/peptide cotransporter (PEPT 2) from human kidney: Functional characterization and chromosomal localization," Biochimica et Biophysica Acta, 1240:1-4 (1995).
Steinhoff et al., "Variable Immune Response Against a Developmentally Regulated Self-Antigen," Journal of Autoimmunity, 12:27-34 (1999).
USPTO Notice of Allowance in U.S. Appl. No. 10/497,900, dated Sep. 8, 2009, 7 pages.
USPTO Notice of Allowance in U.S. Appl. No. 10/497,900, dated Dec. 16, 2009, 5 pages.
USPTO Notice of Allowance in U.S. Appl. No. 10/509,343, dated Sep. 21, 2009, 7 pages.
USPTO Notice of Allowance in U.S. Appl. No. 10/509,343, dated Dec. 9, 2009, 5 pages.
Fish & Richardson P.C., Amendment in Reply to Action dated Mar. 31, 2009 in U.S. Appl. No. 10/550,987, filed Sep. 30, 2009, 6 pages.
USPTO Notice of Allowance in U.S. Appl. No. 10/550,987, dated Nov. 17, 2009, 8 pages.
European Search Report for App. Ser. No. EP 05 72 7975, dated Sep. 11, 2009, 2 pages.
Breyer et al., "Mutational analysis of ligand binding activity of $\beta_2$ adrenergic receptor expressed in Escherichia coli," EMBO J., 9(9):2679-2684 (1990).
Clark, M., "Antibody humanization: a case of the 'Emperor's new clothes'?," Immunol. Today, 21(8):397-402 (2000).
Covitz et al., "Membrane Topology of the Human Dipeptide Transporter, hPEPTI, Determined by Epitope Insertions," Biochemistry, 37:15214-15221 (1998).
Kanamitsu, Kotai Kogaku Nyumon, 33-6 (1994) (English translation included).
Kawaguchi et al., "Gan Chiryo to Syukusyu: Frontiers in Cancer Treatment," 13(1):12-20 (2001).
McLaughlin, "Rituximab: perspective on single agent experience, and future directions in combination trials," Critical Reviews in Oncology/Hematology, 40:3-16 (2001).
Saitoh et al., "Recovery of functional peptide transporter PepT1 in budded baculovirus fraction," Protein Expr. Purif., 46(1):130-135 (2006).
Tada et al., "Complement-dependent cytolysis," Dictionary of Immunology 3rd Edition, 144 (1993).

Tate et al., "Molecular Chaperones Stimulate the Functional Expression of the Cocaine-Sensitive Serotonin Transporter," *J. Biol. Chem.*, 274(25):17551-17558 (1999).

Tsuruo et al., "Inhibition of Multidrug-resistant Human Tumor Growth in Athymic Mice by Anti-P-glycoprotein Monoclonal Antibodies," *Jpn. J. Cancer Res.*, 80:627-631 (1989).

Walker et al., "Substrate upregulation of the human small intestinal peptide transporter, hPepT1," *Journal of Physiology*, 507.3:697-706 (1998).

European Search Report for App. Ser. No. EP 03 73 3287, dated Jun. 22, 2009 (2 pages).

* cited by examiner

```
                                              EcoRI─KOZAK
                                           g aat tcc acc      0
                                             Asn Ser Thr
    ──SEQ ID NO: 3
   ┌atg gta agc gct att gtt│tta tat gtg ctt ttg gcg gcg gcg gcg cat   48
    Met Val Ser Ala Ile Val│Leu Tyr Val Leu Leu Ala Ala Ala Ala His
   └──SEQ ID NO: 4
   ─────────────────────────>
      64F1/ SEQ ID NO: 1 tct gcc ttt gcg gcg gag cac tgc aac gcg caa atg aag acg ggt ccg   96
    Ser Ala Phe Ala Ala Glu His Cys Asn Ala Gln Met Lys Thr Gly Pro tac aag att aaa aac ttg gac att acc ccg ccc aag gaa acg ctg caa  144
    Tyr Lys Ile Lys Asn Leu Asp Ile Thr Pro Pro Lys Glu Thr Leu Gln aag gac gtg gaa atc acc atc gtg gag acg gac tac aac gaa aac gtg  192
    Lys Asp Val Glu Ile Thr Ile Val Glu Thr Asp Tyr Asn Glu Asn Val att atc ggc tac aag ggg tac tac cag gcg tat gcg tac aac ggc ggc  240
    Ile Ile Gly Tyr Lys Gly Tyr Tyr Gln Ala Tyr Ala Tyr Asn Gly Gly tcg ctg gat ccc aac aca cgc gtc gaa gaa acc atg aaa acg ctg aat  288
    Ser Leu Asp Pro Asn Thr Arg Val Glu Glu Thr Met Lys Thr Leu Asn gtg ggc aaa gag gat ttg ctt atg tgg agc atc agg cag cag tgc gag  336
    Val Gly Lys Glu Asp Leu Leu Met Trp Ser Ile Arg Gln Gln Cys Glu gtg ggc gaa gag ctg atc gac cgt tgg ggc agt gac agc gac gac tgt  384
    Val Gly Glu Glu Leu Ile Asp Arg Trp Gly Ser Asp Ser Asp Asp Cys ttt cgc gac aac gag ggc cgc ggc cag tgg gtc aaa ggc aaa gag ttg  432
    Phe Arg Asp Asn Glu Gly Arg Gly Gln Trp Val Lys Gly Lys Glu Leu gtg aag cgg cag aat aac aat cac ttt gcg cac cac acg tgc aac aaa  480
    Val Lys Arg Gln Asn Asn Asn His Phe Ala His His Thr Cys Asn Lys tcg tgg cga tgc ggc att tcc act tcg aaa atg tac agc agg ctc gag  528
    Ser Trp Arg Cys Gly Ile Ser Thr Ser Lys Met Tyr Ser Arg Leu Glu tgc cag gac gac acg gac gag tgc cag gta tac att ttg gac gct gag  576
    Cys Gln Asp Asp Thr Asp Glu Cys Gln Val Tyr Ile Leu Asp Ala Glu ggc aac ccc atc aac gtg acc gtg gac act gtg ctt cat cga gac ggc  624
    Gly Asn Pro Ile Asn Val Thr Val Asp Thr Val Leu His Arg Asp Gly gtg agt atg att ctc aaa caa aag tct acg ttc acc acg cgc caa ata  672
    Val Ser Met Ile Leu Lys Gln Lys Ser Thr Phe Thr Thr Arg Gln Ile aaa gct gcg tgt ctg ctc att aaa gat gac aaa aat aac ccc gag tcg  720
    Lys Ala Ala Cys Leu Leu Ile Lys Asp Asp Lys Asn Asn Pro Glu Ser gtg aca cgc gaa cac tgt ttg att gac aat gat ata tat gat ctt tct  768
    Val Thr Arg Glu His Cys Leu Ile Asp Asn Asp Ile Tyr Asp Leu Ser aaa aac acg tgg aac tgc aag ttt aac aga tgc att aaa cgc aaa gtc  816
    Lys Asn Thr Trp Asn Cys Lys Phe Asn Arg Cys Ile Lys Arg Lys Val
```

FIG. 1

```
gag cac cga gtc aag aag cgg ccg ccc act tgg cgc cac aac gtt aga    864
Glu His Arg Val Lys Lys Arg Pro Pro Thr Trp Arg His Asn Val Arg gcc aag tac aca gag gga gac act gcc acc aaa ggc gac ctg atg cat    912
Ala Lys Tyr Thr Glu Gly Asp Thr Ala Thr Lys Gly Asp Leu Met His att caa gag gag ctg atg tac gaa aac gat ttg ctg aaa atg aac att    960
Ile Gln Glu Glu Leu Met Tyr Glu Asn Asp Leu Leu Lys Met Asn Ile gag ctg atg cat gcg cac atc aac aag cta aac aat atg ctg cac gac   1008
Glu Leu Met His Ala His Ile Asn Lys Leu Asn Asn Met Leu His Asp ctg ata gtc tcc gtg gcc aag gtg gac gag cgt ttg att ggc aat ctc   1056
Leu Ile Val Ser Val Ala Lys Val Asp Glu Arg Leu Ile Gly Asn Leu atg aac aac tct gtt tct tca aca ttt ttg tcg gac gac acg ttt ttg   1104
Met Asn Asn Ser Val Ser Ser Thr Phe Leu Ser Asp Asp Thr Phe Leu ctg atg ccg tgc acc aat ccg ccg gca cac acc agt aat tgc tac aac   1152
Leu Met Pro Cys Thr Asn Pro Pro Ala His Thr Ser Asn Cys Tyr Asn aac agc atc tac aaa gaa ggg cgt tgg gtg gcc aac acg gac tcg tcg   1200
Asn Ser Ile Tyr Lys Glu Gly Arg Trp Val Ala Asn Thr Asp Ser Ser caa tgc ata gat ttt agc aac tac aag gaa cta gca att gac gac gac   1248
Gln Cys Ile Asp Phe Ser Asn Tyr Lys Glu Leu Ala Ile Asp Asp Asp gtc gag ttt tgg atc ccg acc atc ggc aac acg acc tat cac gac agt   1296
Val Glu Phe Trp Ile Pro Thr Ile Gly Asn Thr Thr Tyr His Asp Ser tgg aaa gat gcc agc ggc tgg tcg ttt att gcc caa caa aaa agc aac   1344
Trp Lys Asp Ala Ser Gly Trp Ser Phe Ile Ala Gln Gln Lys Ser Asn ctc ata acc acc atg gag aac acc aag ttt ggc ggc gtc ggc acc agt   1392
Leu Ile Thr Thr Met Glu Asn Thr Lys Phe Gly Gly Val Gly Thr Ser ctg agc gac atc act tcc atg gct gaa ggc gaa ttg gcc gct aaa ttg   1440
Leu Ser Asp Ile Thr Ser Met Ala Glu Gly Glu Leu Ala Ala Lys Leu act tcg ttc atg ttt ggt cat gta gtt aac ttt gta att ata tta att   1488
Thr Ser Phe Met Phe Gly His Val Val Asn Phe Val Ile Ile Leu Ile
                                                    SEQ ID NO: 3◄─┐
gtg att tta ttt ttg tac tgt atg att aga aac cgt aat aga caa tat   1536
Val Ile Leu Phe Leu Tyr Cys Met Ile Arg Asn Arg Asn Arg Gln Tyr
                                            SEQ ID NO: 4◄─┘
                                       ◄┄┄┄┄┄┄┄┄┄┄┄┄┄┄┄┄┄┄┄┄
                                       64R1/ SEQ ID NO: 2
    ┌─EcoRI
taa gaa ttc                                                       1545
 *  Glu Phe
```

FIG. 2

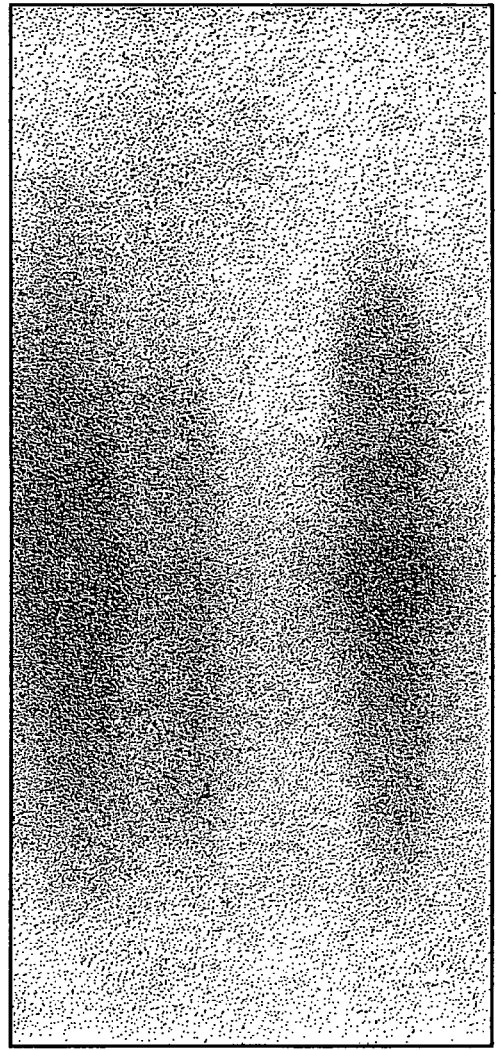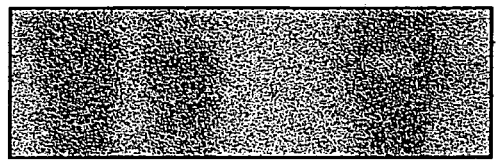
FIG. 5

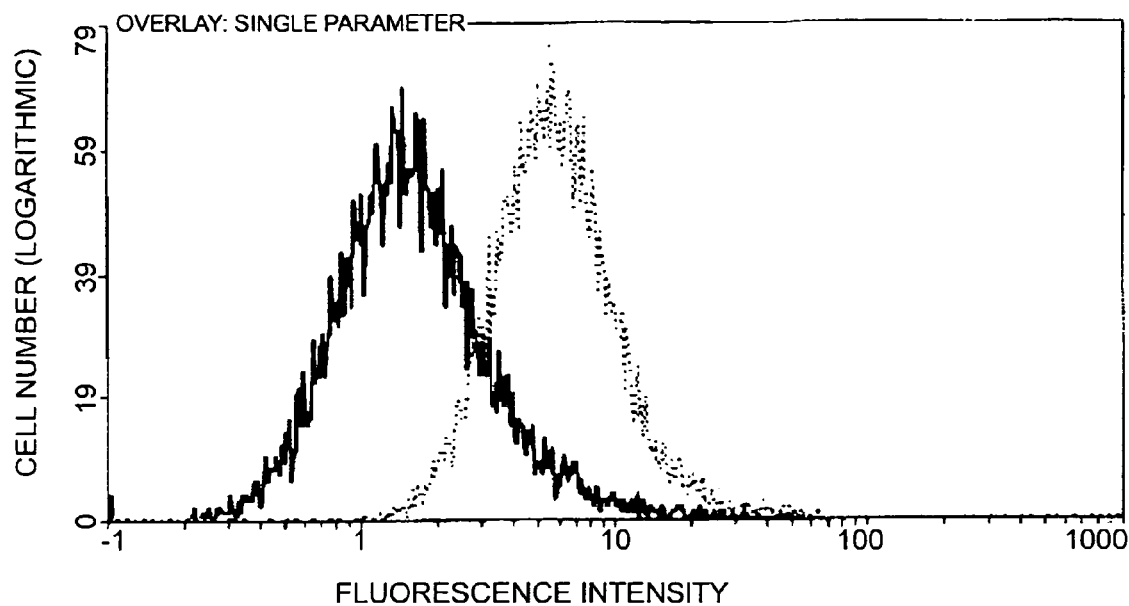
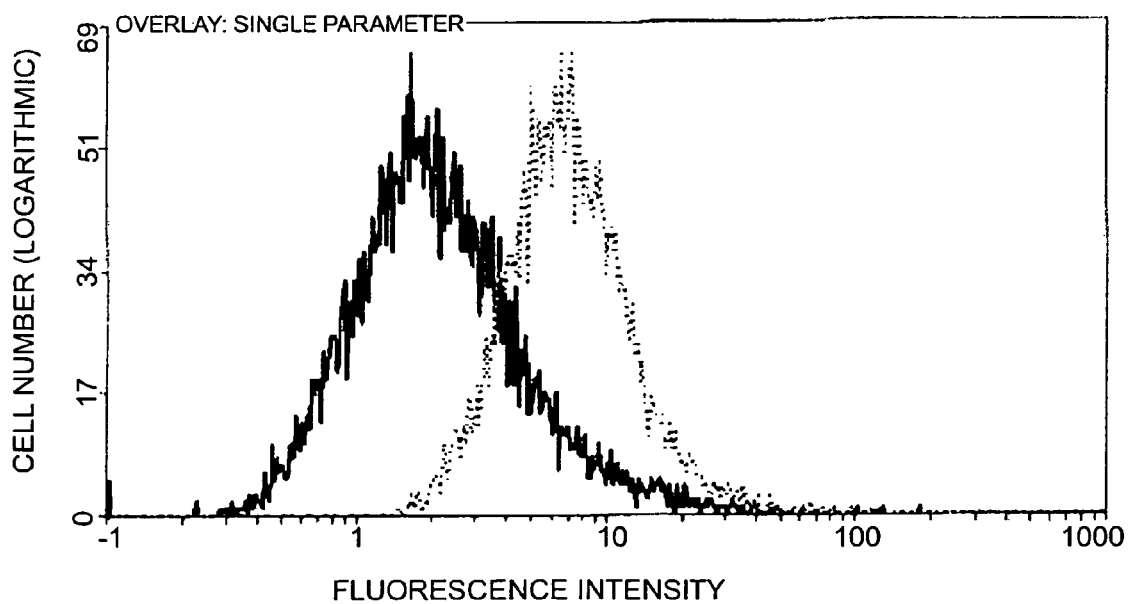
FIG. 8

MOUSE #3
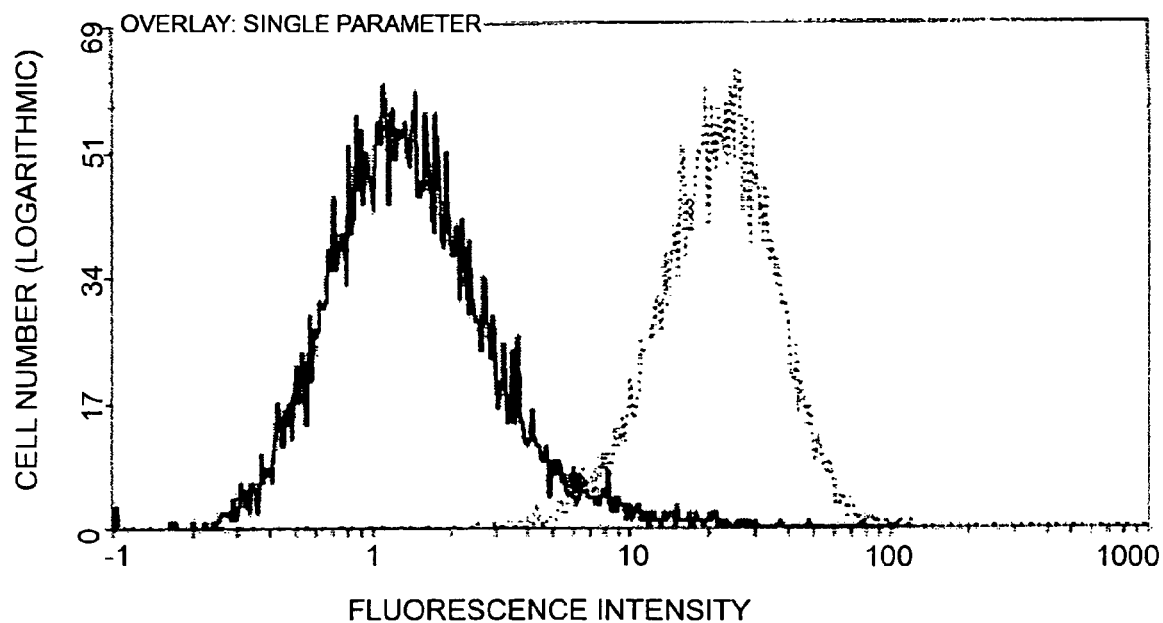
NO ANTIBODY
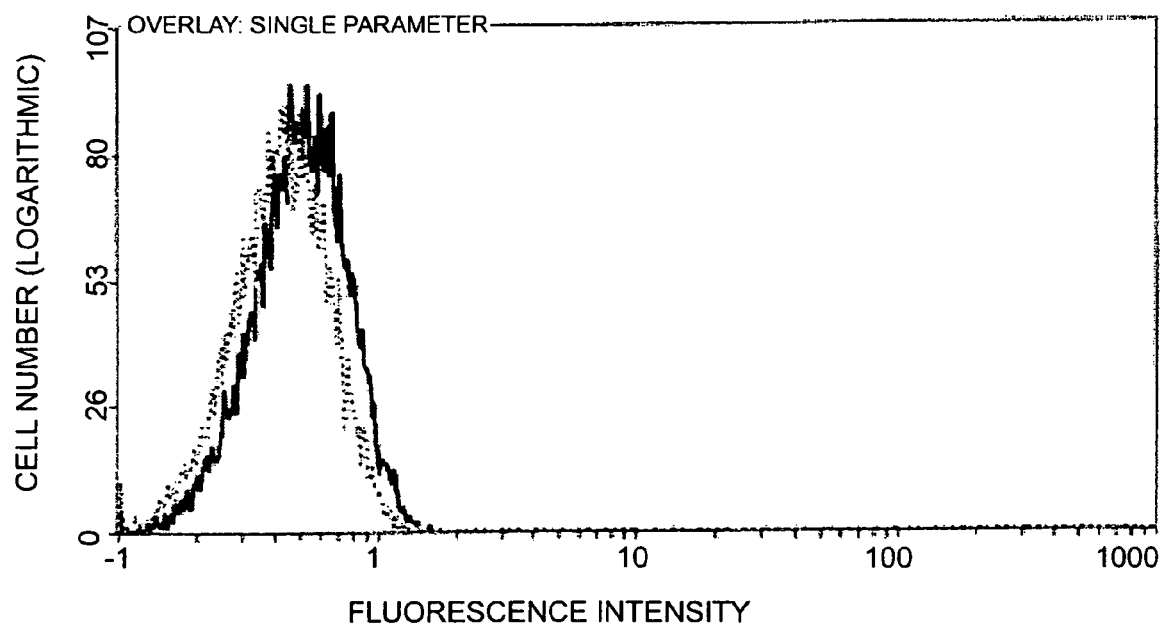
FIG. 9

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 1
gaattccacc atggtaagcg ctattgtt                                            28

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:an
```

-continued artificially synthesized primer sequence

<400> SEQUENCE: 2
gaattcttaa tattgtctat tacggt    26

<210> SEQ ID NO 3
<211> LENGTH: 1539
<212> TYPE: DNA
<213> ORGANISM: Baculovirus
<220> FEATURE:
<221> NAME/KEY: CDS
<222> LOCATION: (1)..(1539)

<400> SEQUENCE: 3

| | | | | | | | | | | | | | | | | |
|---|---|---|---|---|---|---|---|---|---|---|---|---|---|---|---|---|
| atg | gta | agc | gct | att | gtt | tta | tat | gtg | ctt | ttg | gcg | gcg | gcg | gcg | cat | 48 |
| Met | Val | Ser | Ala | Ile | Val | Leu | Tyr | Val | Leu | Leu | Ala | Ala | Ala | Ala | His | |
| 1 | | | | 5 | | | | | 10 | | | | | 15 | | |

| tct | gcc | ttt | gcg | gcg | gag | cac | tgc | aac | gcg | caa | atg | aag | acg | ggt | ccg | 96 |
| Ser | Ala | Phe | Ala | Ala | Glu | His | Cys | Asn | Ala | Gln | Met | Lys | Thr | Gly | Pro | |
| | | | 20 | | | | | 25 | | | | | 30 | | | |

| tac | aag | att | aaa | aac | ttg | gac | att | acc | ccg | ccc | aag | gaa | acg | ctg | caa | 144 |
| Tyr | Lys | Ile | Lys | Asn | Leu | Asp | Ile | Thr | Pro | Pro | Lys | Glu | Thr | Leu | Gln | |
| | | 35 | | | | | 40 | | | | | 45 | | | | |

| aag | gac | gtg | gaa | atc | acc | atc | gtg | gag | acg | gac | tac | aac | gaa | aac | gtg | 192 |
| Lys | Asp | Val | Glu | Ile | Thr | Ile | Val | Glu | Thr | Asp | Tyr | Asn | Glu | Asn | Val | |
| | 50 | | | | | 55 | | | | | 60 | | | | | |

| att | atc | ggc | tac | aag | ggg | tac | tac | cag | gcg | tat | gcg | tac | aac | ggc | ggc | 240 |
| Ile | Ile | Gly | Tyr | Lys | Gly | Tyr | Tyr | Gln | Ala | Tyr | Ala | Tyr | Asn | Gly | Gly | |
| 65 | | | | | 70 | | | | | 75 | | | | | 80 | |

| tcg | ctg | gat | ccc | aac | aca | cgc | gtc | gaa | gaa | acc | atg | aaa | acg | ctg | aat | 288 |
| Ser | Leu | Asp | Pro | Asn | Thr | Arg | Val | Glu | Glu | Thr | Met | Lys | Thr | Leu | Asn | |
| | | | | 85 | | | | | 90 | | | | | 95 | | |

| gtg | ggc | aaa | gag | gat | ttg | ctt | atg | tgg | agc | atc | agg | cag | cag | tgc | gag | 336 |
| Val | Gly | Lys | Glu | Asp | Leu | Leu | Met | Trp | Ser | Ile | Arg | Gln | Gln | Cys | Glu | |
| | | | 100 | | | | | 105 | | | | | 110 | | | |

| gtg | ggc | gaa | gag | ctg | atc | gac | cgt | tgg | ggc | agt | gac | agc | gac | gac | tgt | 384 |
| Val | Gly | Glu | Glu | Leu | Ile | Asp | Arg | Trp | Gly | Ser | Asp | Ser | Asp | Asp | Cys | |
| | | 115 | | | | | 120 | | | | | 125 | | | | |

| ttt | cgc | gac | aac | gag | ggc | cgc | ggc | cag | tgg | gtc | aaa | ggc | aaa | gag | ttg | 432 |
| Phe | Arg | Asp | Asn | Glu | Gly | Arg | Gly | Gln | Trp | Val | Lys | Gly | Lys | Glu | Leu | |
| | 130 | | | | | 135 | | | | | 140 | | | | | |

| gtg | aag | cgg | cag | aat | aac | aat | cac | ttt | gcg | cac | cac | acg | tgc | aac | aaa | 480 |
| Val | Lys | Arg | Gln | Asn | Asn | Asn | His | Phe | Ala | His | His | Thr | Cys | Asn | Lys | |
| 145 | | | | | 150 | | | | | 155 | | | | | 160 | |

| tcg | tgg | cga | tgc | ggc | att | tcc | act | tcg | aaa | atg | tac | agc | agg | ctc | gag | 528 |
| Ser | Trp | Arg | Cys | Gly | Ile | Ser | Thr | Ser | Lys | Met | Tyr | Ser | Arg | Leu | Glu | |
| | | | | 165 | | | | | 170 | | | | | 175 | | |

| tgc | cag | gac | gac | acg | gac | gag | tgc | cag | gta | tac | att | ttg | gac | gct | gag | 576 |
| Cys | Gln | Asp | Asp | Thr | Asp | Glu | Cys | Gln | Val | Tyr | Ile | Leu | Asp | Ala | Glu | |
| | | | 180 | | | | | 185 | | | | | 190 | | | |

| ggc | aac | ccc | atc | aac | gtg | acc | gtg | gac | act | gtg | ctt | cat | cga | gac | ggc | 624 |
| Gly | Asn | Pro | Ile | Asn | Val | Thr | Val | Asp | Thr | Val | Leu | His | Arg | Asp | Gly | |
| | | 195 | | | | | 200 | | | | | 205 | | | | |

| gtg | agt | atg | att | ctc | aaa | caa | aag | tct | acg | ttc | acc | acg | cgc | caa | ata | 672 |
| Val | Ser | Met | Ile | Leu | Lys | Gln | Lys | Ser | Thr | Phe | Thr | Thr | Arg | Gln | Ile | |
| | 210 | | | | | 215 | | | | | 220 | | | | | |

| aaa | gct | gcg | tgt | ctg | ctc | att | aaa | gat | gac | aaa | aat | aac | ccc | gag | tcg | 720 |
| Lys | Ala | Ala | Cys | Leu | Leu | Ile | Lys | Asp | Asp | Lys | Asn | Asn | Pro | Glu | Ser | |
| 225 | | | | | 230 | | | | | 235 | | | | | 240 | |

| gtg | aca | cgc | gaa | cac | tgt | ttg | att | gac | aat | gat | ata | tat | gat | ctt | tct | 768 |
| Val | Thr | Arg | Glu | His | Cys | Leu | Ile | Asp | Asn | Asp | Ile | Tyr | Asp | Leu | Ser | |

```
aaa aac acg tgg aac tgc aag ttt aac aga tgc att aaa cgc aaa gtc      816
Lys Asn Thr Trp Asn Cys Lys Phe Asn Arg Cys Ile Lys Arg Lys Val
                260                 265                 270 gag cac cga gtc aag aag cgg ccg ccc act tgg cgc cac aac gtt aga      864
Glu His Arg Val Lys Lys Arg Pro Pro Thr Trp Arg His Asn Val Arg
            275                 280                 285 gcc aag tac aca gag gga gac act gcc acc aaa ggc gac ctg atg cat      912
Ala Lys Tyr Thr Glu Gly Asp Thr Ala Thr Lys Gly Asp Leu Met His
        290                 295                 300 att caa gag gag ctg atg tac gaa aac gat ttg ctg aaa atg aac att      960
Ile Gln Glu Glu Leu Met Tyr Glu Asn Asp Leu Leu Lys Met Asn Ile
    305                 310                 315                 320 gag ctg atg cat gcg cac atc aac aag cta aac aat atg ctg cac gac     1008
Glu Leu Met His Ala His Ile Asn Lys Leu Asn Asn Met Leu His Asp
                325                 330                 335 ctg ata gtc tcc gtg gcc aag gtg gac gag cgt ttg att ggc aat ctc     1056
Leu Ile Val Ser Val Ala Lys Val Asp Glu Arg Leu Ile Gly Asn Leu
            340                 345                 350 atg aac aac tct gtt tct tca aca ttt ttg tcg gac gac acg ttt ttg     1104
Met Asn Asn Ser Val Ser Ser Thr Phe Leu Ser Asp Asp Thr Phe Leu
        355                 360                 365 ctg atg ccg tgc acc aat ccg ccg gca cac acc agt aat tgc tac aac     1152
Leu Met Pro Cys Thr Asn Pro Pro Ala His Thr Ser Asn Cys Tyr Asn
    370                 375                 380 aac agc atc tac aaa gaa ggg cgt tgg gtg gcc aac acg gac tcg tcg     1200
Asn Ser Ile Tyr Lys Glu Gly Arg Trp Val Ala Asn Thr Asp Ser Ser
385                 390                 395                 400 caa tgc ata gat ttt agc aac tac aag gaa cta gca att gac gac gac     1248
Gln Cys Ile Asp Phe Ser Asn Tyr Lys Glu Leu Ala Ile Asp Asp Asp
                405                 410                 415 gtc gag ttt tgg atc ccg acc atc ggc aac acg acc tat cac gac agt     1296
Val Glu Phe Trp Ile Pro Thr Ile Gly Asn Thr Thr Tyr His Asp Ser
            420                 425                 430 tgg aaa gat gcc agc ggc tgg tcg ttt att gcc caa caa aaa agc aac     1344
Trp Lys Asp Ala Ser Gly Trp Ser Phe Ile Ala Gln Gln Lys Ser Asn
        435                 440                 445 ctc ata acc acc atg gag aac acc aag ttt ggc ggc gtc ggc acc agt     1392
Leu Ile Thr Thr Met Glu Asn Thr Lys Phe Gly Gly Val Gly Thr Ser
    450                 455                 460 ctg agc gac atc act tcc atg gct gaa ggc gaa ttg gcc gct aaa ttg     1440
Leu Ser Asp Ile Thr Ser Met Ala Glu Gly Glu Leu Ala Ala Lys Leu
465                 470                 475                 480 act tcg ttc atg ttt ggt cat gta gtt aac ttt gta att ata tta att     1488
Thr Ser Phe Met Phe Gly His Val Val Asn Phe Val Ile Ile Leu Ile
                485                 490                 495 gtg att tta ttt ttg tac tgt atg att aga aac cgt aat aga caa tat     1536
Val Ile Leu Phe Leu Tyr Cys Met Ile Arg Asn Arg Asn Arg Gln Tyr
            500                 505                 510 taa                                                                  1539

<210> SEQ ID NO 4
<211> LENGTH: 512
<212> TYPE: PRT
<213> ORGANISM: Baculovirus

<400> SEQUENCE: 4

Met Val Ser Ala Ile Val Leu Tyr Val Leu Leu Ala Ala Ala Ala His
  1               5                  10                  15
```

-continued

```
Ser Ala Phe Ala Ala Glu His Cys Asn Ala Gln Met Lys Thr Gly Pro
             20                  25                  30
Tyr Lys Ile Lys Asn Leu Asp Ile Thr Pro Pro Lys Glu Thr Leu Gln
         35                  40                  45
Lys Asp Val Glu Ile Thr Ile Val Glu Thr Asp Tyr Asn Glu Asn Val
     50                  55                  60
Ile Ile Gly Tyr Lys Gly Tyr Tyr Gln Ala Tyr Ala Tyr Asn Gly Gly
 65                  70                  75                  80
Ser Leu Asp Pro Asn Thr Arg Val Glu Thr Met Lys Thr Leu Asn
             85                  90                  95
Val Gly Lys Glu Asp Leu Leu Met Trp Ser Ile Arg Gln Gln Cys Glu
            100                 105                 110
Val Gly Glu Glu Leu Ile Asp Arg Trp Gly Ser Asp Ser Asp Asp Cys
            115                 120                 125
Phe Arg Asp Asn Glu Gly Arg Gly Gln Trp Val Lys Gly Lys Glu Leu
            130                 135                 140
Val Lys Arg Gln Asn Asn Asn His Phe Ala His His Thr Cys Asn Lys
145                 150                 155                 160
Ser Trp Arg Cys Gly Ile Ser Thr Ser Lys Met Tyr Ser Arg Leu Glu
                165                 170                 175
Cys Gln Asp Asp Thr Asp Glu Cys Gln Val Tyr Ile Leu Asp Ala Glu
            180                 185                 190
Gly Asn Pro Ile Asn Val Thr Val Asp Thr Val Leu His Arg Asp Gly
            195                 200                 205
Val Ser Met Ile Leu Lys Gln Lys Ser Thr Phe Thr Thr Arg Gln Ile
    210                 215                 220
Lys Ala Ala Cys Leu Leu Ile Lys Asp Lys Asn Asn Pro Glu Ser
225                 230                 235                 240
Val Thr Arg Glu His Cys Leu Ile Asp Asn Asp Ile Tyr Asp Leu Ser
                245                 250                 255
Lys Asn Thr Trp Asn Cys Lys Phe Asn Arg Cys Ile Lys Arg Lys Val
            260                 265                 270
Glu His Arg Val Lys Lys Arg Pro Pro Thr Trp Arg His Asn Val Arg
            275                 280                 285
Ala Lys Tyr Thr Glu Gly Asp Thr Ala Thr Lys Gly Asp Leu Met His
    290                 295                 300
Ile Gln Glu Glu Leu Met Tyr Glu Asn Asp Leu Leu Lys Met Asn Ile
305                 310                 315                 320
Glu Leu Met His Ala His Ile Asn Lys Leu Asn Asn Met Leu His Asp
                325                 330                 335
Leu Ile Val Ser Val Ala Lys Val Asp Glu Arg Leu Ile Gly Asn Leu
            340                 345                 350
Met Asn Asn Ser Val Ser Ser Thr Phe Leu Ser Asp Thr Phe Leu
    355                 360                 365
Leu Met Pro Cys Thr Asn Pro Pro Ala His Thr Ser Asn Cys Tyr Asn
370                 375                 380
Asn Ser Ile Tyr Lys Glu Gly Arg Trp Val Ala Asn Thr Asp Ser Ser
385                 390                 395                 400
Gln Cys Ile Asp Phe Ser Asn Tyr Lys Glu Leu Ala Ile Asp Asp
                405                 410                 415
Val Glu Phe Trp Ile Pro Thr Ile Gly Asn Thr Thr Tyr His Asp Ser
            420                 425                 430
Trp Lys Asp Ala Ser Gly Trp Ser Phe Ile Ala Gln Gln Lys Ser Asn
```

-continued

```
            435                 440                 445
Leu Ile Thr Thr Met Glu Asn Thr Lys Phe Gly Gly Val Gly Thr Ser
    450                 455                 460

Leu Ser Asp Ile Thr Ser Met Ala Glu Gly Glu Leu Ala Ala Lys Leu
465                 470                 475                 480

Thr Ser Phe Met Phe Gly His Val Val Asn Phe Val Ile Ile Leu Ile
                485                 490                 495

Val Ile Leu Phe Leu Tyr Cys Met Ile Arg Asn Arg Asn Arg Gln Tyr
                500                 505                 510
```

METHODS FOR PRODUCING ANTIBODY

CLAIM OF PRIORITY

This application is the National Stage of International Application No. PCT/JP03/07071, filed Jun. 4, 2003, which claims the benefit of Japanese Patent Application Serial Nos. 2002-164834, filed on Jun. 5, 2002, and 2002-180351, filed on Jun. 20, 2002, the entire contents of which are hereby incorporated by reference.

1. Technical Field

This invention relates to methods for producing antibodies. This invention also relates to the antibodies obtained by the methods of this invention. This invention further relates to transgenic non-human animals useful for the production of antibodies generated by the methods of this invention.

2. Background Art

Antibodies are useful as therapeutic agents, diagnostic agents, or reagents for various diseases. Many kinds of antibodies have been isolated to date. General methods for producing antibodies comprise the steps of administering antigens to mammals such as mice; and obtaining antibodies derived from the serum of these animals. However, subject antibodies are not always obtained efficiently by antibody production methods, as in the following cases, for example:

when a small quantity of antigen is used to immunize mammals; or when an insufficiently purified antigen is used to immunize mammals.

Therefore, when immunizing, it is desirable to prepare a large quantity of a sufficiently purified antigen. Practically, however, many antigens are difficult to purify or to sufficiently prepare. Thus, the step of antigen preparation has often prevented antibody production.

Membrane proteins are one example of antigens for which immunogens are difficult to prepare. Generally, membrane proteins are often difficult to highly express or sufficiently purify. These difficulties have been an obstacle in obtaining antibodies against membrane proteins.

Attention has been paid to methods that use baculoviruses to express large quantities of membrane proteins. By introducing a gene that encodes a subject membrane protein into a baculovirus genome, the subject membrane protein is expressed on the membrane surface of the budding baculovirus. (WO 98/46777, Unexamined Published Japanese Patent Application No. (JP-A) 2001-333773). Using these methods enables expression of a large quantity of a subject membrane protein on a viral membrane surface.

However, in addition to exogenous membrane proteins, baculovirus-derived membrane proteins are also expressed on the membrane surface of the baculoviruses thus obtained. Thus, when budding baculoviruses are used as antigens, antibodies against baculovirus-derived membrane proteins may also be produced. Accordingly, it has been difficult to efficiently produce antibodies against subject membrane proteins by using known immunization methods.

For example, immunization using budding baculoviruses as antigens often induces antibodies that recognize gp64. The membrane proteins of baculoviruses comprise large quantities of gp64. In addition, due to gp64's high antigenicity, immunized animals can easily recognize gp64 as "nonself". Consequently, budding baculoviruses can be thought to preferentially induce anti-gp64 antibodies.

Therefore, when using membrane proteins as antigens, the subject membrane proteins expressed on the baculovirus membrane surface must be sufficiently purified. However, purifying exogenous membrane proteins from budding baculoviruses is generally difficult. Thus, it can be said that sufficient quantities of highly purified membrane proteins cannot be practically obtained for use in immunization. Using conventional methods to obtain target antibodies for these difficult-to-purify antigens has been difficult.

DISCLOSURE OF THE INVENTION

An objective of the present invention is to solve the above-described problems. In other words, an objective of this invention is to provide methods for producing antibodies that enable target antibodies to be easily obtained. In addition, an objective of this invention is to provide transgenic non-human animals that efficiently produce subject antibodies.

To solve the above-described problems, the inventors focused on antigens that are comprised in immunogens and that interfere with the production of subject antibodies. Then, the inventors thought that a subject antibody could be easily obtained by using immunized animals whose immune response to such interfering antigens is repressed. Furthermore, the inventors found that the above-described problems can be solved by utilizing immunotolerance to the antigens that interfere with production of the subject antibodies, to control the immune responses of the immunized animals, and thereby complete the present invention.

Specifically, the present invention relates to methods for producing antibodies, transgenic non-human animals useful for these methods, and methods for producing these non-human animals. Specifically, the present invention provides the following:

[1] A method for producing an antibody that recognizes a target antigen, wherein the method comprises the steps of:
i) immunizing a non-human animal that has immunotolerance to a background antigen comprised in an immunogen, wherein the immunogen comprises both the target antigen and the background antigen; and
ii) obtaining an antibody against the target antigen, or a gene encoding the antibody.

[2] The method of [1], wherein immunotolerance is induced artificially.

[3] The method of [1], wherein the non-human animal is a transgenic non-human animal.

[4] A method for producing an antibody against a target antigen, wherein the method comprises the steps of:
(a) preparing an immunogen comprising the target antigen and a background antigen;
(b) producing a transgenic non-human animal comprising a gene expressibly encoding the background antigen;
(c) administering the immunogen of (a) to the transgenic non-human animal of (b); and
(d) isolating the antibody against the target antigen from the transgenic non-human animal.

[5] The method of [4], wherein the immunogen is a virus particle or a part thereof.

[6] The method of [5], wherein the virus is a baculovirus.

[7] The method of [4], wherein the target antigen is a membrane protein.

[8] The method of [6], wherein the background antigen is gp64.

[9] The method of [4], wherein the non-human animal is a mouse.

[10] An antibody that is produced by the method of any one of [1] to [9].

[11] A chimeric antibody between a non-human animal and human, or a humanized antibody, produced using the antibody of [10].

[12] A transgenic non-human animal, into which a gene encoding a viral envelope protein is introduced.

[13] The transgenic non-human animal of [12], wherein the virus is a baculovirus.

[14] The non-human animal of [13], wherein the viral envelope protein is gp64.

[15] The non-human animal of [12], wherein the non-human animal is a mouse.

[16] The non-human animal of [12] for use in producing an antibody against an antigen comprising a viral protein.

[17] A method for producing a non-human immunized animal, wherein the method comprises the step of producing a transgenic non-human animal into which a gene encoding a background antigen is introduced.

[18] A non-human immunized animal for obtaining an antibody against a target antigen comprising a background antigen, wherein the animal is produced by the method of [17].

[19] A method for producing an antibody against PepT1, wherein the method comprises the steps of:
(a) preparing a baculovirus that expressibly comprises a DNA which encodes PepT1 or a fragment thereof;
(b) infecting a host cell with the baculovirus of (a) to obtain a budding virus that expresses PepT1 or a fragment thereof;
(c) producing a transgenic non-human animal that expressibly comprises a gene encoding a baculovirus membrane protein gp64;
(d) immunizing the transgenic non-human animal of (c) with a fraction comprising the budding virus of (b) or PepT1 or its fragment; and
(e) recovering the antibody-recognizing PepT1 from the immunized animal.

This invention relates to methods for producing antibodies which recognize target antigens, wherein the methods comprise the step of immunizing immunogens that comprise a target antigen and a background antigen, to non-human animals with immunotolerance to the background antigen comprised in the immunogen.

The term "target antigen" denotes antigens recognized by subject antibodies. The target antigens can be selected from any compound comprising antigenicity. Specifically, proteins, sugar chains, lipids, or inorganic substances are known to comprise antigenicity. The target antigens may be naturally occurring or artificially synthesized. The artificially synthesized target antigens comprise recombinant proteins prepared by genetic engineering technology, and many kinds of chemically-synthesized organic compounds.

According to the present invention, the term "background antigen" denotes substances comprising antigenic determinants for which antibody generation is not desired, or denotes the antigenic determinants themselves. For example, any antigenic substance that is not a target antigen, but which is contaminated within the target antigen, is a background antigen. Typical background antigens are proteins contaminated within crudely purified target antigens. More specifically, host cell-derived proteins in a recombinant protein are examples of background antigens. The term "background antigen" may also be defined to mean antigens that are comprised within an immunogen for inducing subject antibody generation, and that induce production of a non-subject antibody.

Generally, a background antigen is an antigenic substance other than a target antigen. According to the present invention, however, antigenic determinants present on target antigen molecules may also be referred to as background antigens. For example, if an antigenic determinant for which antibody generation is undesired is present on a target antigen molecule, the antigenic determinant is defined as a background antigen. Moreover, the background antigens of the present invention include substances that comprise antigenic determinants as background antigens, yet do not comprise target antigens.

According to the present invention, preferable background antigens are proteins, peptides, sugars, or glycoproteins. Of these, proteins or peptides are particularly preferable background antigens. The term "peptide" denotes, for example, polypeptides that consist of 100 or fewer amino acid residues. The term "protein" includes "peptide".

According to the present invention, the term "immunotolerance" denotes a condition in which an immune response, specific to an antigen that is an immunotolerance target (an immunotolerance antigen), is lost or decreased. When the level of a subject's immune response to an immunotolerance antigen is reduced compared to that of a normal immunized animal, the subject can be regarded to comprise immunotolerance against the immunotolerance antigen. For example, when the amount of an antibody generated against an immunotolerance antigen is decreased in response to the administration of an immunotolerance antigen, the level of immune response is then considered to be low. Immunotolerance levels are not limited.

In addition, the term "immunotolerance antigen" denotes antigenic substances for which a subject's immune response is decreased. Also, according to the present invention, a reduced level of a specific immune response to an immunotolerance antigen denotes that the degree by which the immune response to the immunotolerance antigen has decreased is greater than for other antigens. Thus, even if the immune response to antigens other than the immunotolerance antigen is decreased, immunotolerance has been established if the level of decrease in immune response to other antigens is less than the level of decrease for the immunotolerance antigen. Also, according to the present invention, immunotolerance includes cases of immunotolerance to antigenic substances other than background antigens. Subjects which are immunotolerant to multiple antigens may also be used in the present invention, as long as they have an immune response to a target antigen. On the other hand, cases of immunodeficiency where the level of actual immune response is decreased are not preferable, since generation of antibodies against target antigens cannot be expected.

In the present invention, non-human animals that comprise immunotolerance to a background antigen are used as immunized animals. Non-human animals comprising artificially induced immunotolerance are preferably used. For example, non-human animals comprising immunotolerance can be generated as below:

First, a gene encoding a background antigen can be introduced into a non-human animal to generate a transgenic animal that comprises the gene encoding the background antigen. Transgenic animals thus obtained have immunotolerance to the expression product of the introduced gene (the background antigen). Immunotolerance can also be induced by multiple administrations of an immunotolerance antigen (a background antigen) to non-human animals in the fetal stage or shortly after birth.

Methods for administering antigens as immunotolerance antigens to non-human animals in the fetal stage or shortly after birth can include methods for administering the antigenic substances themselves into non-human animals. Alternatively, indirect methods for administering immunotolerance antigens may also be applied. For example, subject immunotolerance antigens are administered by in vivo expression of genes that encode the immunotolerance antigens. Such methods include methods for directly administering an antigen-coding DNA (naked DNA methods), for transplanting antigen-expressing cells into non-human animals, methods using viral vectors, and methods using DNA vaccines.

Of these methods, transgenic non-human animals which preserve a gene encoding an immunotolerance antigen in an expressible state are preferred as the non-human animals comprising immunotolerance of the present invention. The transgenic animals comprise in their body an immunotolerance antigen that was originally an exogenous protein prior to the maturation of immune functions. Therefore, it is highly possible that the immune functions of the transgenic animals recognize the immunotolerance antigen as being completely endogenous. Thus, the use of such transgenic non-human animals is advantageous in inducing immunotolerance in the present invention. The transgenic animals, into which immunotolerance antigens are introduced, produce few antibodies to immunotolerance antigens, as shown in Example 8.

In addition, the immunotolerant traits of the transgenic animals can be inherited by their progeny. Therefore, once a transgenic non-human animal has been established for the present invention, immunized animals comprising the same traits can be stably provided.

This invention also relates to transgenic non-human animals into which genes encoding a viral envelope protein are introduced to produce antibodies against antigens comprising the viral proteins. Moreover, this invention relates to use of transgenic non-human animals in which a gene encoding the viral envelope protein is expressibly maintained, as immunized animals for producing antibodies against antigens comprising viral envelope proteins. Furthermore, this invention relates to methods for producing non-human immunized animals, where the methods comprise the step of generating a transgenic non-human animal into which a gene encoding a background antigen has been introduced.

Many kinds of transgenic non-human animals into which different kinds of genes have been introduced are known in the art. However, animals into which an exogenous gene encoding a background antigen has been introduced are not known to be useful as immune animals for a target antigen that comprises a background antigen.

Since an animal in which a gene that encodes a target antigen protein has been deleted, (so called knock-out animals), does not comprise the target antigen protein congenitally, an antibody against the target antigen can be obtained by administering the target antigen to the knock-out animal, even if the target antigen is highly homologous to a protein present in the immunized animal. Moreover, it is possible to obtain an animal which is deficient in a target antigen, and which expresses an immunotolerant antigen, by crossing the target antigen-deficient animal with the transgenic animal of the present invention.

Genes coding for background antigens can also be introduced into a fetal or post-fetal non-human animal in a fetal period or thereafter, by using naked DNA methods, DNA vaccine methods, or methods for transplanting cells that express background antigens. Non-human animals thus obtained are also included in the transgenic non-human animals of the present invention.

There is no limitation as to the number of background antigens used to induce immunotolerance in the immunotolerant non-human animals of the present invention. That is, a non-human animal, in which immunotolerance to at least one background antigen has been induced, can be used in an antibody-production method of the present invention. Non-human animals in which immunotolerance to multiple background antigens has been induced can also be used as immunized animals.

In the immunized animals, it is not always important to suppress production of antibodies against all of the background antigens that might be comprised in an immunogen. Production of antibodies that recognize background antigens is acceptable as long as they do not interfere with the production and isolation of an antibody against a target antigen. Therefore, for example, an immunized animal in which immunotolerance has only been induced to a major background antigen can be used as a preferable immunized animal in the present invention.

In the present invention, non-human animals comprise, for example, monkeys, pigs, dogs, rats, mice, and rabbits. For example, rodents such as rats, mice, and hamsters are preferable as non-human animals. To induce immunotolerance by preparing transgenic animals, it is advantageous to use non-human animals which mature fast and for which gene manipulation technologies have been established, such as rodents. Mice in particular are non-human animals that meet these requirements at a high level.

This invention relates to transgenic non-human animals into which genes coding for viral envelope proteins have been introduced. Transgenic non-human animals of the present invention are useful in immunization against a target antigen in the presence of viral envelope proteins. Typically, viral envelope proteins in this invention are proteins that make up an envelope of a budding virus. In baculoviruses, for example, the protein called gp64 is an envelope protein.

For example, a transgenic non-human animal with immunotolerance to the baculoviral gp64 is useful as an immune animal for an immunogen produced by the baculovirus expression system. Many kinds of proteins can be produced by the baculovirus expression system. Therefore, by using these transgenic animals and baculovirus expression systems in combination, target antibodies can be easily obtained by using a variety of protein antigens as target antigens.

Immunogens of the present invention comprise both target antigens and background antigens. As described above, there is no particular limitation as to the substances constituting target antigens or background antigens. When an animal with immunotolerance is produced by introduction of a gene encoding a background antigen, the background antigen is a protein. Immunogens may include substances other than target antigens and background antigens.

Furthermore, there is no limitation as to the types of background antigens that comprise the immunogens of the present invention. Therefore, immunogens comprising multiple kinds of background antigens, which may interfere with the production of antibodies against a target antigen, can also be used in the present invention. The presence of these background antigens is not a problem, as long as an immunized animal shows immunotolerance to each background antigen. Alternatively, background antigens which do not substantially interfere with the production of antibodies against a target antigen may be comprised in an immunogen, regardless of whether or not an immunized animal is immunotolerant to them.

Generally, a target antigen comprises substances derived from biological materials. Biological materials are complex mixtures comprising various components. Thus, target antigens are usually prepared using various mixtures as starting materials. Therefore, it is difficult to obtain highly-purified target antigens. In other words, it involves a lot of time and effort to isolate a large quantity of a highly pure target antigen.

Practically, it is almost inevitable that an immunogen contains substances other than the target antigen.

Immunogens of the present invention specifically include cells, cell cultures, cell lysates, viruses, or unpurified antigens. Parts of cells or viruses can be used as immunogens, as well as whole cells or whole viruses. For example, cell membranes or virus envelopes can be used as immunogens. When a cell or virus is used as an immunogen, a gene coding for a subject antigen can be artificially introduced into the cell or virus by recombinant gene technology that artificially expresses the subject antigen.

One preferable immunogen of the present invention is a viral particle or part thereof. Viruses are comprised of relatively simple components, including nucleic acids, and limited proteins, saccharides, and such. Consequently, the types of background antigens that may interfere with target antigen isolation are also limited. In sum, inducing immunotolerance against a limited number of background antigens in an animal to be immunized would be enough to carry out a method for producing antigen of the present invention.

In the present invention, baculoviruses, for example, are preferred among the viruses that can be used as immunogens. Baculoviruses are insect viruses that comprise a structure whereby a double-stranded DNA genome is covered with a capsid protein. Expression systems using Nucleopolyhedrovirus (NPV), a type of baculovirus, are useful as systems for expressing exogenous genes. NPV comprises strong promoter activity. Therefore, any protein can be produced in large quantities by inserting an exogenous gene into the NPV genome. Specifically, strong expression of any exogenous gene is induced by recombinantly substituting the gene coding for the protein called polyhedron with the exogenous gene.

Any exogenous genes can be introduced into a baculovirus. For example, a gene encoding a membrane protein can be used as an exogenous gene.

By using baculoviruses, a subject membrane protein can be expressed along with a viral envelope protein in a form that retains that structure. Another big advantage of the baculovirus expression system is that the expressed products are easily recovered as budding viral particles.

Membrane proteins include many biologically important molecules, such as receptors and transporters. However, many membrane proteins maintain their structure by being located in a cell membrane. In addition, membrane proteins are often post-translationally modified with sugar chains or lipids. Therefore, there are often cases where expression systems utilizing prokaryotes such as E. coli cannot reproduce membrane proteins in their in situ structure.

As methods for expressing exogenous proteins such as membrane proteins on viral envelopes, for example, the method of WO98/46777 or Loisel et al. for expressing envelope proteins using budding baculoviruses can be used (Loisel, T. P. et al., Nature Biotech. 15: 1300-1304 (1997)). More specifically, a recombinant vector for insect cells comprising a gene encoding an exogenous protein is constructed, and inserted, along with baculoviral DNA, into insect cells such as Sf9. The exogenous protein encoded by the recombinant vector is then expressed on mature viral particles (virions), which are released by infected cells to the outside of cells prior to infected cell death. Recombinant viruses that express the exogenous protein can thus be obtained.

In the present invention, a budding virus is a virus that is released from infected cells by budding. Generally, viruses covered with an envelope can bud from cells infected with these viruses, and are released continuously, even when the cells have not been destroyed. On the other hand, adenoviruses that are not covered by an envelope, and herpes viruses that are covered by a nuclear envelope, are released from the cells all at once, upon cell destruction. Budding viruses are particularly preferable in the present invention. In addition, those skilled in the art can suitably select hosts to be infected with a recombinant virus, depending on the type of virus used, so long as viral replication is possible in the host. For example, insect Sf9 cells can be used when using baculoviruses. Generally, protein expression systems using baculoviruses and insect cells can be useful because modifications such as fatty acid acetylation or glycosylation are carried out at the same time as translation or post-translation, in the same way as in mammalian cells. In addition, the expression level of heterologous proteins in such systems is greater than that in mammalian cell systems (Luckow V. A. and Summers M. D., Virol. 167: 56 (1988)).

The viruses expressing exogenous proteins can be obtained by, for example, culturing a host that has been infected with a recombinant virus comprising a gene that encodes an exogenous protein. Alternatively, using methods such as the above-mentioned methods of WO 98/46777 and Loisel et al (Loisel, T. P. et al., Nature Biotech. 15: 1300-1304 (1997)), a recombinant vector encoding an exogenous protein can be inserted into an insect cell along with a baculovirus, and exogenous proteins can be expressed on the envelope of the baculovirus released outside of the cell. In addition, using methods like that of Strehlow et al. (D. Strehlow et al., Proc. Natl. Acad. Sci. USA. 97: 4209-4214 (2000)), packaging cells such as PA317 can be infected with recombinant Moloney murine leukemia viruses, which are constructed using vectors derived from Moloney viruses introduced with exogenous protein-encoding genes, and the exogenous proteins can be expressed on the envelope of viruses released outside of the cells. However, the viruses of the present invention that express exogenous proteins, useful as immunogens, are not limited to those that are constructed using the above methods.

Recombinant viruses constructed as described above can be purified using known methods. For example, known methods for purifying viruses include augmented density gradient centrifugation (Albrechtsen et al., J. Virological Methods 28: 245-256 (1990); Hewish et al., J. Virological Methods 7: 223-228 (1983)), size exclusion chromatography (Hjorth and Mereno-Lopez, J. Virological Methods 5: 151-158 (1982); Crooks et al., J. Chrom. 502: 59-68 (1990); Mento S. J. (Viagene, Inc.) 1994 Williamsburg Bioprocessing Conference), affinity chromatography using monoclonal antibodies, sulphated fucose-containing polysaccharides and the like (Najayou et al., J. Virological Methods 32: 67-77 (1991); Diaco et al., J. Gen. Virol. 67: 345-351 (1986); Fowler, J. Virological Methods 11: 59-74 (1986); TOKUSAIHYOU No. 97/032010 (Unexamined Publication of Japanese National Phase Patent Application)), and DEAE ion exchange chromatography (Haruna et al., Virology 13: 264-267 (1961)). Thus, purification can be carried out using the above methods or combinations thereof.

In the present invention, there is no limitation as to the kind of background antigen which becomes an immunotolerance antigen for use as an antigen to induce immunotolerance in immune animals. Preferably, the immunotolerance antigens are such substances that are comprised in an immunogen in a large quantity, or that have a strong antigenicity. For example, when a baculovirus is used as an immunogen, gp64 is preferably used as an immunotolerance antigen. Gp64 is a major background antigen, which is expressed in large quantities on the surface of the viral envelope, and which is susceptible to being recognized as non-self by animals immunized with baculoviruses.

Baculoviruses comprise characteristics that are preferable in an expression system for exogenous proteins. On the other hand, use of an expression product produced by this system as an immunogen, it is accompanied by production of background antigens, which can be a drawback. In particular, when using a baculovirus expression system to produce a membrane protein that is used as an immunogen, the presence of gp64 is a big problem. gp64 is comprised in large amounts in viral envelope proteins. Thus, contamination of an exogenous membrane protein with gp64 is inevitable.

By using the antibody-production methods of the present invention, the inhibitory effect that background antigens have on the acquisition of antibodies against a target antigen can be suppressed. Consequently, the use of this invention enables sufficient application of the advantages of a baculovirus expression system as an exogenous protein expression system, even in the preparation of immunogens.

In the present invention, naturally occurring viruses or parts thereof can also be used as immunogens. Development of an antibody that recognizes a specific antigenic determinant of a naturally occurring virus is important to the specific detection of the virus, and also to prevention of or therapy for infection by that virus. Whereas antibodies against major antigens can be easily produced, it is often difficult to acquire an antibody that recognizes a specific antigenic determinant. This situation is common to the above described case in which a baculovirus expression product is used as an immunogen.

When using a naturally occurring virus as an immunogen of the present invention, a gene coding for a protein that will act as a background antigen, selected from proteins that constitute the virus, is introduced into a non-human animal to prepare a transgenic animal. Alternatively, viral particles themselves, or parts thereof that comprise a target antigen, are used as immunogens. In this way, an antibody that recognizes a target antigen can be efficiently obtained.

For example, the surface antigens of influenza viruses are important antigens that determine the viral strain. If antibodies that recognized the surface antigens specific to each influenza virus strain could be easily obtained, this would be useful to identification of the virus, as well as in the prevention of or therapy for infection by the virus. However, when using the viral particles themselves as immunogens, antibodies that recognize structures common to the viruses will also be produced in large quantities.

Antibodies that recognize surface antigens specific to each viral strain can be efficiently obtained by using a transgenic non-human animal of the present invention, which has immunotolerance to an envelope protein that is common to the influenza viruses. In other words, this invention can be also carried out using surface antigens that are specific to each strain of a virus as target antigens, and using structures that are common to the viruses as background antigens.

A preferable embodiment of the antibody-production methods of the present invention is described below. In this embodiment, membrane proteins are used as target antigens. For example, human-derived membrane proteins can be used as the membrane proteins.

First of all, a target protein is expressed on the surface of the baculovirus envelope, and this baculovirus is used as an immunogen. As a method for expression the membrane protein using baculoviruses, for example, the methods for expressing membrane proteins using budding baculoviruses, disclosed in WO 98/46777, JP-A 2001-333773, Loisel et al. (T. P. Loisel et al., Nature Biotech. 15: 1300-1304 (1997)), can be used.

In more detail, a recombinant vector for insect cells is constructed to comprise a gene encoding a membrane protein. This vector is then introduced into insect cells along with the baculovirus DNA. Sf9 cells and such are used as the insect cells. The membrane protein encoded by the recombinant vector is expressed in mature viral particles (virions) released extracellularly from the infected cells prior to cell death. Therefore, budding baculovirus particles that express the membrane protein (target antigen) may be obtained by harvesting mature virus particles. Methods for recovering budding baculovirus from cultured cells are also known in the art. The thus obtained budding baculoviruses that express a membrane protein (target antigen) are used as immunogens of the present invention.

As described above, the surface of the baculovirus envelope expresses not only a membrane protein (the target antigen), but also another envelope protein derived from a baculovirus. In particular, gp64 is expressed in large quantities on the surface of baculoviruses, and also has strong antigenicity. Therefore, when immunization is carried out using a budding baculovirus, anti-gp64 antibodies are also produced, and thus antibodies to the membrane protein (target antigen) cannot be efficiently obtained.

Accordingly, in the present invention, an animal that expresses gp64 is used as an animal to be immunized. Specifically, a transgenic animal that expresses gp64 is produced by introducing a vector that comprises a gene encoding gp64 into an animal. The transgenic animals of the present invention are non-human animals. For example, a transgenic mouse into which the gp64 gene has been introduced can be used as an animal to be immunized in the present invention.

In the present invention, these transgenic mice are immunized with the budding baculovirus particles obtained as described above. Since the gp64-expressing transgenic mice endogenously express gp64, they comprise immunotolerance to gp64, which acts as a background antigen. In other words, production of anti-gp64 antibodies in the gp64-expressing transgenic mice is suppressed when the mice are immunized with the budding baculovirus particles. As a result, antibodies against a target membrane protein can be produced efficiently.

Methods for producing transgenic mice are known in the art. For example, transgenic mice can be obtained according to the methods described in Proc. Natl. Acad. Sci. USA 77: 7380-7384 (1980). Specifically, subject genes are introduced into mammalian totipotent cells, and then the cells are brought up into individuals. A subject transgenic mouse can be obtained from the individuals thus obtained by screening for individuals in which the introduced gene has been integrated into both somatic cells and germ cells. Fertilized eggs, early embryos, and cultured cells with multipotency such as ES cells, and such, can be used as the totipotent cells for introducing a gene.

More specifically, transgenic mice can be prepared, for example, by the method in Example 2.

The antibody-production methods of the present invention can be used to produce polyclonal and monoclonal antibodies. Polyclonal antibodies can be obtained by recovering antibodies to the target antigen from an immunized animal. Alternatively, monoclonal antibody-producing cells can be obtained by cloning an antibody-producing cell derived from an immunized antimal.

Furthermore, by using antibodies or genes thereof obtained from an immunized animal such as mice, chimeric antibodies of human and immunized animals, or humanized antibodies can be obtained. Methods for producing these antibodies that comprise modified structures are also known in the art.

Furthermore, this invention relates to the antibodies obtained by the methods of the present invention. The antibodies of the present invention comprise any kind of antibody that can be obtained by a procedure comprising a method as described above. Consequently, this invention includes, for example, monoclonal antibodies, polyclonal antibodies, chimeric antibodies of human and immunized animals, humanized antibodies, and human antibodies. For example, a transgenic mouse whose immune system has been substituted with that of a human is known in the art. Human antibodies can be obtained by immunizing such mice.

Preferable antibodies in the present invention are antibodies that recognize human membrane proteins. Many membrane proteins are important as target molecules for drug discovery. However, antibodies specific to membrane proteins have been considered difficult to obtain due to purification difficulties. The present invention, however, has made it possible to efficiently obtain a subject antibody, even though the target antigen is a recombinantly-produced membrane protein that co-exists with a background antigen. For example, as a membrane protein, PepT1 is an important molecule. The nucleotide sequence and amino acid sequence of PepT1 are already known: human PepT1 (GenBank XM_007063) is described in J. Biol. Chem. 270(12): 6456-6463 (1995); and mouse PepT1 (GenBank AF205540) is described in Biochim. Biophys. Acta. 1492: 145-154 (2000)).

Those anti-PepT1 antibodies that bind to an extracellular region of PepT1 are useful. In particular, an antibody that specifically binds to an extracellular region of PepT1 is preferable in the present invention. In the present invention, the phrase "specifically binds to an extracellular region" means the ability to immunologically discriminate extracellular regions of PepT1 from other regions. More specifically, an antibody that specifically binds to an extracellular region of PepT1 is defined as an antibody that binds to an extracellular region, but does not bind, for example, to an intracellular region or transmembrane domain of PepT1. Human PepT1 is a preferable PepT1 in the present invention. Human PepT1 includes not only PepT1s derived from humans, but also recombinant PepT1s obtained by expressing human PepT1 in a baculovirus expression system.

The human PepT1 molecules that are used as immunogens do not have to be entire molecules, as long as they retain a target antigen structure. For example, a fragment comprising a PepT1 extracellular region can be used as an immunogen. A preferable PepT1 in the present invention is a human PepT1 that comprises transport activity, or a full-length human PepT1. A full-length human PepT1 comprising transport activity is especially preferable. The transport activity of a human PepT1 can be detected by using the activity of incorporating a substrate into a cell as an indicator. As its substrates, PepT1 is known to incorporate glycylsarcosine or such into cells. Incorporation of glycylsarcosine can be assayed by using [$^{14}$C] glycylsarcosine or such.

Human PepT1 is preferably expressed on the surface of a membrane (such as a viral envelope or cell membrane). The transport activity of a PepT1 expressed on the surface of a viral envelope can be detected by contacting a solution comprising viral particles with a substrate; and then monitoring the incorporation of the substrate into the viral particles.

Well-known methods can be used for the methods of immunizing to obtain antibodies. Animals can be immunized with an immunogen using known methods. General methods include injecting a sensitizing antigen into a mammal by subcutaneous or intraperitoneal injection. Specifically, an immunogen is diluted with an appropriate volume of Phosphate-Buffered Saline (PBS) or physiological saline, and as desired, the suspension is mixed with an appropriate volume of a conventional adjuvant. This is emulsified and applied to the mammals. For example, Freund's complete adjuvant can be used as an adjuvant. In addition, after this, an immunogen that has been mixed with an appropriate volume of Freund's incomplete adjuvant is preferably applied several times every four to 21 days.

When immunizing an immunogen, an appropriate carrier can also be used. In this way immunization occurs, and the increased level of a desired antibody in the serum can be confirmed using conventional methods.

When obtaining the target antibodies, an increase in the level of a desired antibody in the serum is confirmed, and blood is then collected from the immunized mammals. Serum can be separated from collected blood using known methods. As polyclonal antibodies, serum comprising polyclonal antibodies can be used. Where necessary, fractions comprising polyclonal antibodies can be isolated from this serum, and this fraction can also be used.

For example, fractions only recognizing the target antigens can be obtained using affinity columns coupled to the target antigens. Immunoglobulin G or M can be prepared by purifying these fractions using a protein A or protein G column.

After confirming the increase in the level of the intended antibody in the serum of a mammal that was sensitized by the above-described antigen, the antibody-producing cells are extracted from the mammal and cloned to obtain monoclonal antibodies. Spleen cells and such can be used as antibody-producing cells. Antibody-producing cells can be cloned by cell fusion methods. Mammalian myeloma cells and such can be used as parent cells to be fused with the above-mentioned antibody-producing cells. Even more preferably, myeloma cells that comprise unique auxotrophy or drug resistance can be examples of useful selective markers for fusion cells (hybridoma cells).

By basically following the methods known in the art, fusion cells can be obtained from the antibody-producing cells and the myeloma cells described above. Methods for producing monoclonal antibodies by using the cell fusion techniques have been established, for example, by Milstein et al. (Galfre, G. and Milstein, C., Methods Enzymol. (1981) 73, 3-46).

The hybridoma cells produced by cell fusion techniques are selected by culturing in a selective medium. A suitable selective medium can be used in accordance with the characteristic features of the myeloma cells used for the cell fusion. HAT medium (a medium comprising hypoxanthine, aminopterine, and thymidine), for example, can be used as a selective medium. The hybridoma cells are cultured in the HAT medium for a time sufficient to kill all cells other than the intended hybridoma cells (e.g. all non-fused cells). Generally, hybridoma cells can be selected by continuing culture for several days to several weeks. After selection, a standard limiting dilution method can be used to screen and clone the hybridoma cells that produce the subject antibodies.

Subsequently, the hybridoma cells thus obtained are intraperitoneally transplanted into mice to obtain ascites fluid comprising the monoclonal antibodies. Monoclonal antibodies can also be purified from the ascites fluid. For example, monoclonal antibodies can be purified by ammonium sulfate precipitation methods, protein A or protein G columns, DEAE ion exchange chromatography, or affinity columns coupled with a target antigen.

In addition to producing antibodies by using hybridomas, antibody-producing cells such as antibody-producing sensitized lymphocytes and such, which have been immortalized using oncogenes or viruses and such, can also be used. Epstein-Barr virus (EBV) and so on can be used as a virus for immortalizing cells.

Monoclonal antibodies obtained in this way can also be used as recombinant antibodies that were produced using gene recombination technologies (for example, see Borrebaeck, C. A. K. and Larrick, J. W., Therapeutic Monoclonal Antibodies, UK, Macmillan Publishers Ltd., 1990). Recombinant antibodies can be produced by cloning the DNAs that encode them from antibody-producing cells, such as hybridomas and antibody-producing sensitized lymphocytes, then incorporating these DNAs into a suitable vector, and introducing this vector into a host. The present invention also encompasses such recombinant antibodies.

The antibodies obtained by the methods of the present invention can also be antibody fragments, modified antibodies, and the like. For example, an antibody fragment can be an Fab, F(ab')2, Fv, or a single chain Fv (scFv) where the Fvs of an H chain and L chain are linked by a suitable linker (Huston, J. S. et al., Proc. Natl. Acad. Sci. U.S.A., (1998) 85, 5879-5883). Specifically, the antibody fragments can be obtained by treating antibodies with an enzyme such as papain or pepsin. Alternatively, genes encoding these antibody fragments are constructed, inserted into an expression vector, and expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Antibodies bound to various molecules such as polyethylene glycols (PEG), can also be used as the modified antibodies. "Antibody" in the present invention also encompasses these modified antibodies. Such modified antibodies can be obtained by chemically modifying obtained antibodies. These methods have already been established in the art.

In addition, methods for obtaining human antibodies are known. A target antibody can be obtained by immunizing transgenic animals, that comprise the entire repertoire of human antibody genes, with a target antigen (see, International Patent Application No. WO 93/12227, WO 92/03918, WO 94/02602, WO 94/25585, WO 96/34096, and WO 96/33735).

The antibodies obtained by the methods of the present invention can be chimeric antibodies comprising non-human antibody-derived variable regions, derived from the immunized animals, and human antibody-derived constant regions. In addition, they can also be humanized antibodies comprising non-human antibody-derived complementarity determining regions (CDRs) which are derived from the immunized animals, human antibody-derived framework regions (FRs), and constant regions.

These modified antibodies can be produced using known methods. Specifically, for example, a chimeric antibody is an antibody comprising the antibody heavy chain and light chain variable regions of an immunized animal, and the antibody heavy chain and light chain constant regions of a human. A chimeric antibody can be obtained by (1) ligating a DNA encoding a variable region of an immunized animal-derived antibody to a DNA encoding a constant region of a human antibody; (2) incorporating this into an expression vector; and (3) introducing the vector into a host for production of the antibody.

A humanized antibody, which is also called a reshaped human antibody, is a modified antibody. A humanized antibody is constructed by transplanting a complementarity determining region (CDR) of an antibody of an immunized animal, into the CDR of a human antibody. Conventional genetic recombination techniques for the preparation of such antibodies are known.

Specifically, a DNA sequence designed to ligate a mouse antibody CDR with a human antibody framework region (FR) is synthesized by PCR, using several oligonucleotides constructed to comprise overlapping portions at their ends. A humanized antibody can be obtained by (1) ligating the resulting DNA to a DNA which encodes a human antibody constant region; (2) incorporating this into an expression vector; and (3) transfecting the vector into a host to produce the antibody (see, European Patent Application No. EP 239, 400, and International Patent Application No. WO 96/02576). Those human antibody FRs that are ligated via the CDR, such that the CDR forms a favorable antigen-binding site, are selected. As necessary, amino acids in the framework region of an antibody variable region may be substituted such that the CDR of a reshaped human antibody forms an appropriate antigen-binding site (Sato, K. et al., Cancer Res. (1993) 53, 851-856).

Furthermore, genes coding for the antibodies can be isolated from the antibody-producing cells of an immunized animal. Methods used to isolate genes that code for antibodies are not limited. For example, genes coding for antibodies can be obtained by amplification using the PCR method, by using as templates those genes that code for variable regions, CDRs, or the like. Primers for the amplification of genes that code for antibodies are known in the art. Subject antibodies can be produced by expressing genes thus obtained in an appropriate expression system. Alternatively, the genes obtained by the present invention can be used to produce various modified antibodies, as described above.

Antibodies obtained as above can be purified until they are homogenous immunoglobulin molecules. These purification methods are not particularly limited. Separation and purification methods conventionally used for polypeptides can be used to separate and purify the antibodies used in the present invention. For example, immunoglobulins can be separated and purified by appropriately selecting and combining chromatography columns such as affinity chromatography columns, filters, ultrafiltration, salt precipitation, dialysis, SDS polyacrylamide gel electrophoresis, isoelectric focusing and so on (Antibodies: A Laboratory Manual. Ed Harlow and David Lane, Cold Spring Harbor Laboratory, 1988). The concentration of the above-obtained antibodies can be determined by measuring absorbance, or by enzyme-linked immunosorbent assays (ELISA), etc.

Protein A columns, protein G columns, and such can be used as the columns for use in affinity chromatography. For example, Hyper D, POROS, Sepharose F.F. (Pharmacia) and so on are examples of the columns using protein A.

Examples of chromatography other than affinity chromatography include ion exchange chromatography, hydrophobic chromatography, gel filtration, reverse chromatography, and adsorption chromatography (Strategies for Protein Purification and Characterisation: A Laboratory Course Manual. Ed Daniel R, Marshak et al., Cold Spring Harbor Laboratory Press, 1996). These chromatographies can be carried out using liquid phase chromatography such as HPLC and FPLC.

BRIEF DESCRIPTION OF THE DRAWINGS

FIGS. 1 and 2 show the nucleotide sequence of the constructed gp64 gene.

FIG. 5 is a photograph showing the result of mRNA expression analysis by Northern blotting. In this figure, H, B, I, and M refer to heart, brain, intestine, and muscle, respectively.

FIG. 8 shows the result of FACS analysis of the antibody titer for PepT1-specific antibody in the mouse serum. In this figure, the x-axis and y-axis respectively represent cell number (log scale) and fluorescence intensity. (Above) mouse #1; (below) mouse #2.

FIG. 9 shows the results of the same analysis in FIG. 8. (Above) mouse #3; (below) no antibody.

BEST MODE FOR CARRYING OUT THE INVENTION

The present invention is specifically described herein below using Examples, however, it is not to be construed as being limited thereto.

EXAMPLE 1

Construction of gp64 Transgenic Vector

The nucleotide sequence of gp64 and the amino acid sequence encoded by the gp64 gene are shown in SEQ ID NOs: 3 and 4, respectively (GenBank Acc No. 9627742). PCR was carried out using the gp64 gene as a template, and using the following primer set: the 5' primer 64F1 (SEQ ID NO: 1), which comprises an EcoRI recognition sequence and the KOZAK sequence at its 5' terminus; and the 3' primer 64R1 (SEQ ID NO: 2), which comprises an EcoRI recognition sequence at its 5' terminus (FIGS. 1 and 2). The PCR conditions are shown below:

The PCR reaction solution composition was 5 μl of ×10 ExTaq buffer, 4 μl of dNTP supplied with ExTaq, 1 μl of 10 μmol/l 64F1 primer, 1 μl of 10 μmol/l 64R1 primer, 1 μl of 500 pg/μl pBac-N-blue, 0.5 μl of 5 units/μl ExTaq, and 37.5 μl of deionized water (DIW). PCR was carried out for:

5 minutes at 94° C.;

25 cycles of "15 seconds at 94° C., 30 seconds at 57° C., and 30 seconds at 72° C.";

7 minutes at 72° C.; and

4° C. forever.

The amplified band was subcloned into pGEM-Teasy, and then transformed E. coli DH5α cells. After performing colony PCR using T7 and SP6 primers, the nucleotide sequence of clones confirmed to comprise the insert was analyzed with the ABI Prism® 377 DNA sequencer (Applied Biosystems) and the BigDye® Terminator Cycle Sequencing kit (Applied Biosystems), in combination with the T7 primer or the SP6 primer. As a result, clones comprising the subject gene were confirmed. A fragment comprising the gp64 gene and confirmed to comprise no mutations in its nucleotide sequence was isolated from the clones by EcoRI digestion, and then inserted into an EcoRI-digested pCAGGS1. The resulting vector was used to transform E. coli DH5α cells. Cells comprising the clone as designed were incubated in 250 ml of LB medium at 37° C. overnight, and purified by using the Endofree MAXI kit (QIAGEN) to obtain 581.6 μg of plasmid.

EXAMPLE 2

Introduction of the Gene

Figure 3:
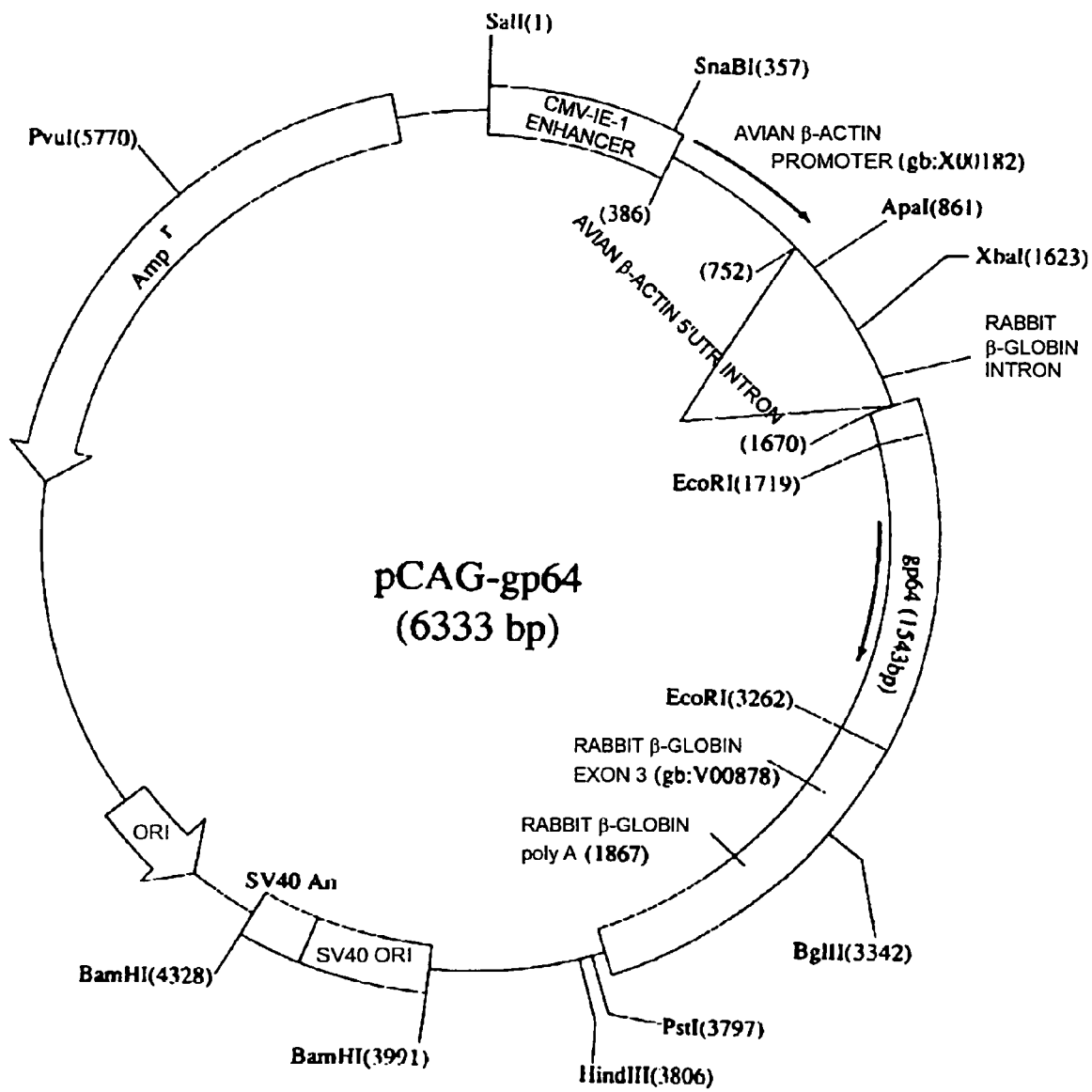
FIG. 3 shows the structure of the pCAG-gp64 vector constructed in Example 1.

The DNA fragment for injection was prepared as follows: The pCAGGS vector into which the gp64 gene was inserted (pCAG-gp64, FIG. 3) was treated with SalI and PstI to yield a fragment (about 3.8 kb) comprising the gp64 gene. This fragment (about 3.8 kb) was extracted using the Gel Extraction kit (QIAGEN), and then diluted with PBS to a concentration of 3 ng/μl, yielding the DNA fragment for injection.

The mouse pronuclear eggs to be injected with the DNA fragment were collected as follows: Specifically, BALB/c series female mice (Nippon CLEA) were induced to superovulate by intraperitoneal administration of 5 international units of pregnant mare serum gonadotrophin (PMSG), followed by intraperitoneal administration of 5 i.u of human chorionic gonadotrophin (hCG) 48 hours later. These female mice were mated with male mice of the same lineage. The morning after mating, the oviducts of female mice that were confirmed to have a vaginal plug were perfused to recover pronuclear eggs.

The DNA fragments were injected into the pronuclear eggs with a micromanipulator (Experimental Medicine (Jikken Igaku) suppl. The latest technologies in gene targeting (gene targeting no saishin gijyutu) (Yodosha), 190-207, 2000). The DNA fragments were injected into 373 embryos of BALB/c mice. On the next day, 216 embryos that had developed to the two-cell stage were transplanted into the oviducts of recipient female mice, which were in the first day of pseudopregnancy, at a density of around ten embryos per oviduct (i.e. around 20 embryos per mouse).

The recipient female mice that did not give birth to offspring by the expected date of delivery were subjected to caesareans, and the resultant offspring were brought up by a foster parent. The results are summarized in Table 1. Fifty offspring were obtained, four of which were transgenic mice into which the gp64 gene has been introduced (referred to as Tgm below). Hereinafter, the transgenic mice obtained in the first generation are described as "Founder" mice.

TABLE 1

| | Viable embryos after injection/ Embryos receiving injection | Transplanted embryos | Implanted embryos | Offspring (female, male) | Weaned Offspring (female, male) | Founder |
|---|---|---|---|---|---|---|
| 1st | 59/63 | 55 | 20 | 9 (4, 5) | 9 (4, 5) | 0 |
| 2nd | 186/223 | 161 | 57 | 26 (13, 13) | 25 (13, 12) | Male 3 |
| 3rd | 61/87 | 56 | 35 | 15 (9, 6) | 15 (9, 6) | Male 1 |
| Total | 306/373 | 216 | 107 | 50 (25, 25) | 49 (25, 24) | Male 4 |

All of the four Founder mice were male. Two lines (Nos. 30 and 31) of these four resulted in four and 20 offspring (F1 mice), respectively. The F1 mice thus obtained were genotyped, and three offspring in line 30 were found to be Tgm, indicating inheritance of the gp64 gene to the second generation. On the other hand, in line 31, all 20 offspring were found to be wild type mice (non-Tgm), in which the gp64 gene could not be detected. Accordingly, the gp64 gene was considered to be integrated into the line 31 Founder mouse in a mosaic structure. Founder mice of lines 34 and 46 had no fertility properties, and therefore, offspring were not obtained. Although the Founder mouse of line 30 impregnated one recipient female immediately after the initiation of crossing, no further offspring was obtained after that (Table 2).

TABLE 2

| Line No. | Date of birth | Sex | Copy Number of the introduced gene | Offspring obtained (date of birth, | total offspring, and Tgm) | | Notes |
|---|---|---|---|---|---|---|---|
| 30 | 010709 | Male | More than 10 copies | 010926 | Female 3, Male 1 | Female 3 | No offspring were obtained after the first delivery. Testes are small and sperm are not observed. |
| 31 | 010709 | Male | 2 to 3 copies | 010927 | Female 3, Male 5 | 0 | Mosaic for gene transfer |
| | | | | 011022 | Male 2 | 0 | |
| | | | | 011108 | Female 4, Male 6 | 0 | |
| 34 | 010709 | Male | 2 to 3 copies | No fertility properties | — | — | Testes are small and sperm are not observed. |
| 46 | 010821 | Male | 2 to 3 copies | No fertility properties | — | — | Testes are small and sperm are not observed. |

Figure 4:
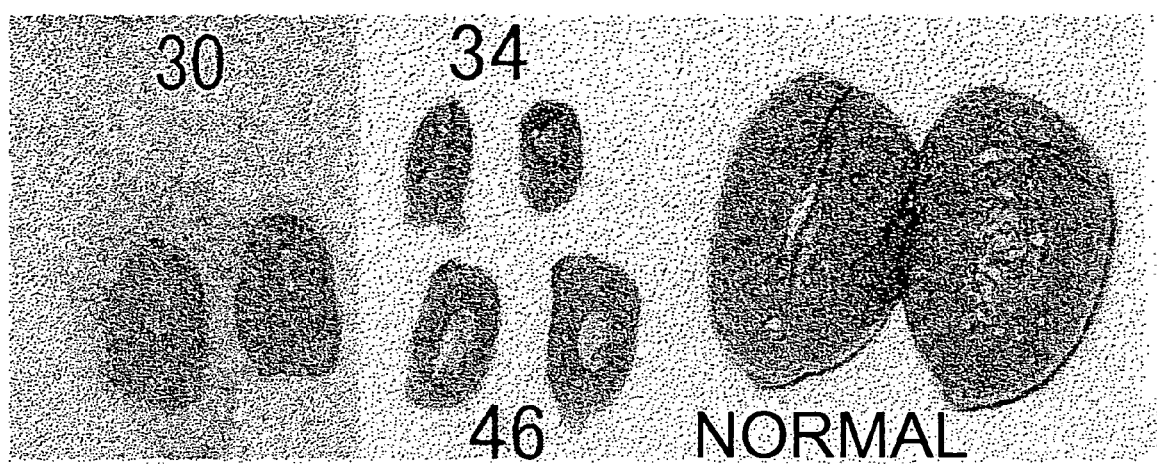
FIG. 4 is a photograph of the Founder mice testes. In this figure, "30", "34", "46" and "Normal" indicate the testes from the Founder mice of lines 30, 34 and 46, and from a normal mouse, respectively.

Consequently, sperm from the Founder mice of lines 30, 34, and 46 was extracted in order to carry out in vitro fertilization. The testes of all three Founder mice were abnormally small (FIG. 4), and no sperm was observed in their cauda epididymidis. Thus in vitro fertilization could not be achieved. From these results, the gp64 protein was found to affect the spermatogenic ability of mice. Therefore, it may be possible to use gp64 in contraception and such.

EXAMPLE 3

Confirmation of the Introduced Gene

DNA was extracted from tails of three week-old mice using an automated nucleic acid isolation system (KURABO), and the presence of the introduced gene was confirmed by Southern blotting method and PCR. The introduced gene was confirmed by Southern blotting, as follows: First, 15 μg of genome DNA was digested with EcoRI, subjected to electrophoresis, and transferred to a nylon membrane. Then, the presence of the introduced gene was confirmed by hybridizing the transferred DNA with a probe, which was about 1.5 kb of EcoRI-digested fragment of pCAG-gp64 vector that comprises the gp64 gene. The presence of the introduced gene was also confirmed by the PCR method, using about 100 ng of DNA as a template, and primers comprising the sequences as shown below:

```
Sense primer 64F1:
GAATTCCACCATGGTAAGCGCTATTGTT;     (SEQ ID NO: 1)

and

Antisense primer 64R1:
GAATTCTTAATATTGTCTATTACGGT.       (SEQ ID NO: 2)
```

PCR was carried out for:

5 minutes at 94° C.;

35 cycles of "15 seconds at 94° C., 30 seconds at 57° C., and 30 seconds at 72° C.";

7 minutes at 72° C.; and

4° C. forever.

The PCR products thus obtained were subjected to electrophoresis to confirm the introduced gene using the presence or absence of a band corresponding to about 1.5 kb as an indicator.

EXAMPLE 4

Confirmation of the Expression of the gp64 Gene in gp64 Tgm

In the line 30 Founder mouse in which inheritance of the gp64 gene to the second generation had been confirmed, expression of the gp64 gene was confirmed by Northern blotting analysis. Specifically, total RNA was extracted from four kinds of organ, heart, brain, intestine, and a thigh muscle, by using ISOGEN (Nippon Gene). Then, 20 µg of the total RNA was subjected to electrophoresis, and was transferred to a nylon membrane. An about 1.5 kb of EcoRI-digested fragment of pCAG-gp64 vector—that comprises the gp64 gene was used as the probe for the Northern blotting analysis. An around 1.5 kb band corresponding to the gp64 gene was expected from the vector construct.

FIG. 5 shows these results. Expression of the gp64 gene was confirmed at least in heart, brain, and thigh muscle. The reason why the bands were seen as three bands is unknown.

EXAMPLE 5

Fertility Properties of the Line 30 Female Tgm (Crossing of Mice)

When the line 30 female Tgm turned eight weeks-old, they were crossed with a male mouse of the same lineage.

As a result, a total of 31 (14 females and 17 males) offspring (F2) were obtained from two deliveries by each of the three F1 female mice (Table 3). 14 of these offspring (five females and nine males) were Tgm. Since offspring were also obtained from the third delivery, the female Tgm were shown to have normal fertility properties.

TABLE 3

| Sex | Individual Number | Number of Deliveries | Offspring (Non-Tgm) | Offspring (Tgm) |
| --- | --- | --- | --- | --- |
| Female | 1 | 2 | Female 3, Male 1 | Female 1, Male 6 |
| Female | 2 | 2 | Female 4, Male 3 | Female 2, Male 1 |
| Female | 3 | 2 | Female 2, Male 4 | Female 2, Male 2 |

EXAMPLE 6

Preparation of Budding Baculoviruses Expressing PepT1

Budding baculoviruses expressing PepT1 and used as immunogens were prepared as follows: PepT1 is a membrane protein that acts as a transporter. The PepT1 structure is known in the art (GenBank XM_007063, J. Biol. Chem. 270(12): 6456-6463 (1995)).

A full-length PepT1 gene was isolated from a human kidney library using PCR. By inserting the full-length human PepT1 gene into pBlueBacHis2A (Invitrogen), the pBlueBacHis-PepT1 transfer vector was constructed. A Bac-N-Blue transfection kit (Invitrogen) was then used to introduce this transfer vector into Sf9 cells, along with Bac-N-Blue DNA. Thus, a recombinant virus for the expression of human PepT1 was constructed. Specifically, 4 µg of pBlueBacHis-PepT1 was added to Bac-N-Blue DNA, and then 1 mL of Grace's medium (GIBCO) and 20 µL of cell FECTIN reagent was added. This was mixed, incubated for 15 minutes at room temperature, and then added drop-by-drop to $2\times10^6$ Sf9 cells washed once with Grace's medium. After incubating for four hours at room temperature, 2 mL of complete medium (Grace's medium which comprises 10% fetal bovine serum (Sigma), 100 units/mL penicillin, and 100 µg/mL streptomycin (GIBCO-BRL)) was added and cultured at 27° C. Recombinant viruses for expressing human PepT1, which were constructed by homologous recombination, were cloned twice according to the instructions attached to the kit. A virus stock of the recombinant viruses was thus obtained.

Construction of budding-type viruses that express human PepT1 was carried out as follows: Specifically, 500 mL of Sf9 cells ($2\times10^6$/mL) were infected with the recombinant viruses prepared as above, so as to achieve MOI=5. After culturing at 27° C. for three days, the culture supernatant was centrifuged for 15 minutes at 800×g, and the cells and cell debris were removed. The supernatant recovered by centrifugation was centrifuged at 45,000×g for 30 minutes, and the precipitate was then suspended in PBS. The cellular components were removed by centrifuging for another 15 minutes at 800×g. The supernatant was again centrifuged at 45,000×g for 30 minutes, and the precipitate was again suspended in PBS. This suspension was the budding virus fraction. Expression of PepT1 in the virus and on the Sf-9 cell membrane was confirmed by Western analysis using anti-His antibodies. In addition, protein concentration was measured using Dc Protein Assay kit (Bio-Rad), with BSA as the standard.

EXAMPLE 7

Immunization of Mice

Mice were immunized by subcutaneous injection with an immunogen, which was emulsified according to the standard method using complete and incomplete Freund's adjuvants (Difco). Injection doses in the first and the second immunizations were 1 mg/mouse and 0.5 mg/mouse, respectively. The second immunization was given 14 days after the first immunization. Seventeen days after the first immunization, serum samples were taken from the mice by retro-orbital bleeding.

EXAMPLE 8

Confirmation of Immunotolerance to gp64 by Western Blotting Analysis

PepT1 expressing budded baculovirus (PepT1-BV) (1 µg/lane) was subjected to SDS-PAGE analysis on 12% gel under reducing conditions. After the electrophoresis, proteins were electroblotted onto a polyvinylidene difluoride (PVDF) membrane. This membrane was reacted with 1,000 fold-diluted serum samples, sequentially washed, and then reacted with a 1,000 fold-diluted Biotin-Anti-Mouse IgG(γ) (Zymed) and Streptavidin-Alkaline Phosphatase (Zymed). An alkaline phosphatase staining kit (Nakarai Tesque) was used for staining. A positive control antibody for detecting gp64 was purchased from NOVAGEN.

Figure 6:
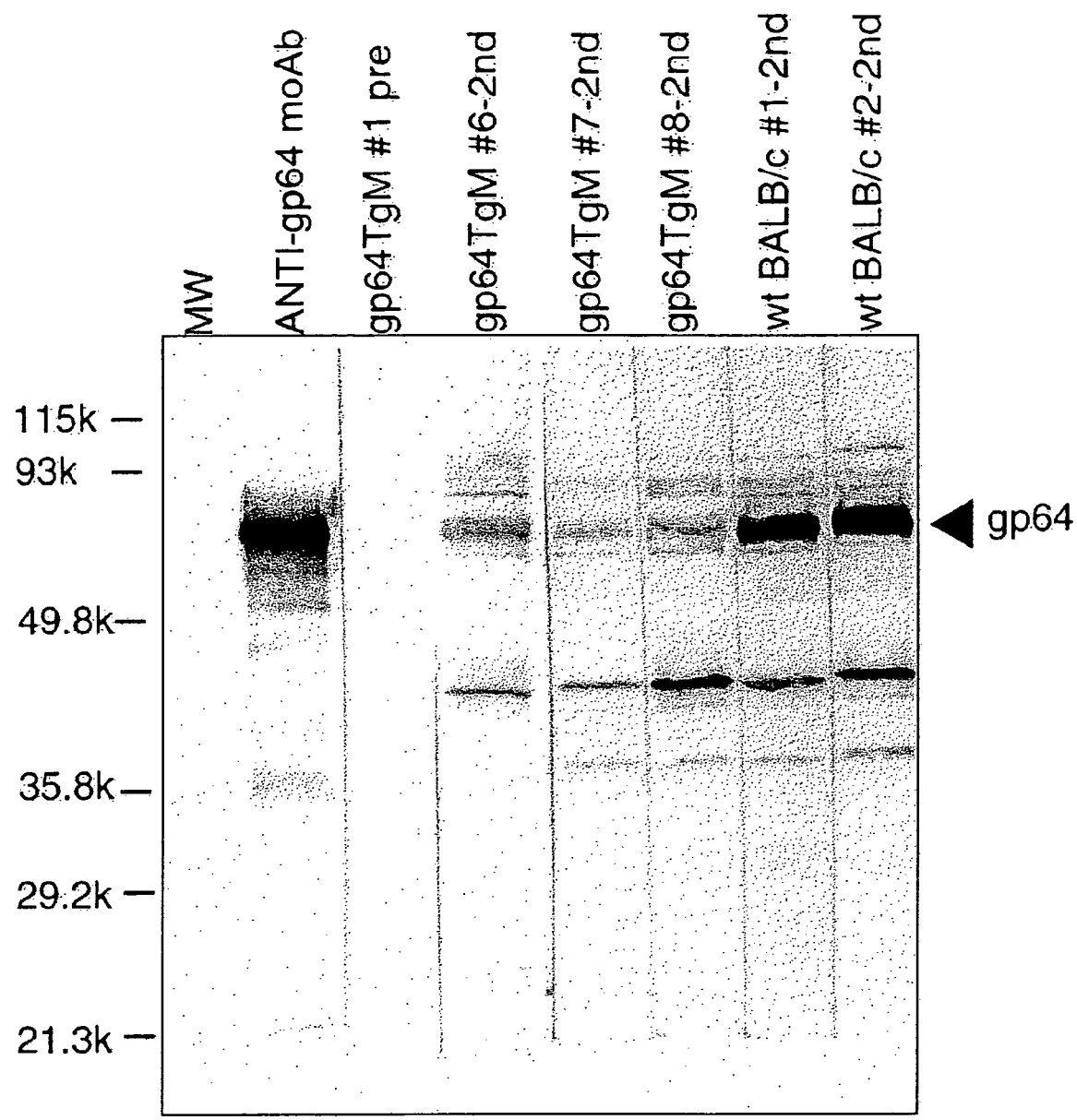
FIG. 6 is a photograph showing the results of Western blotting analysis using anti-mouse IgG. In this figure, "pre" and "2nd" respectively refer to pre-immunization blood collection, and blood collection after the second immunization. Gp64TgM and wtBALB/c represent transgenic and non-transgenic mice, respectively.
Figure 7:
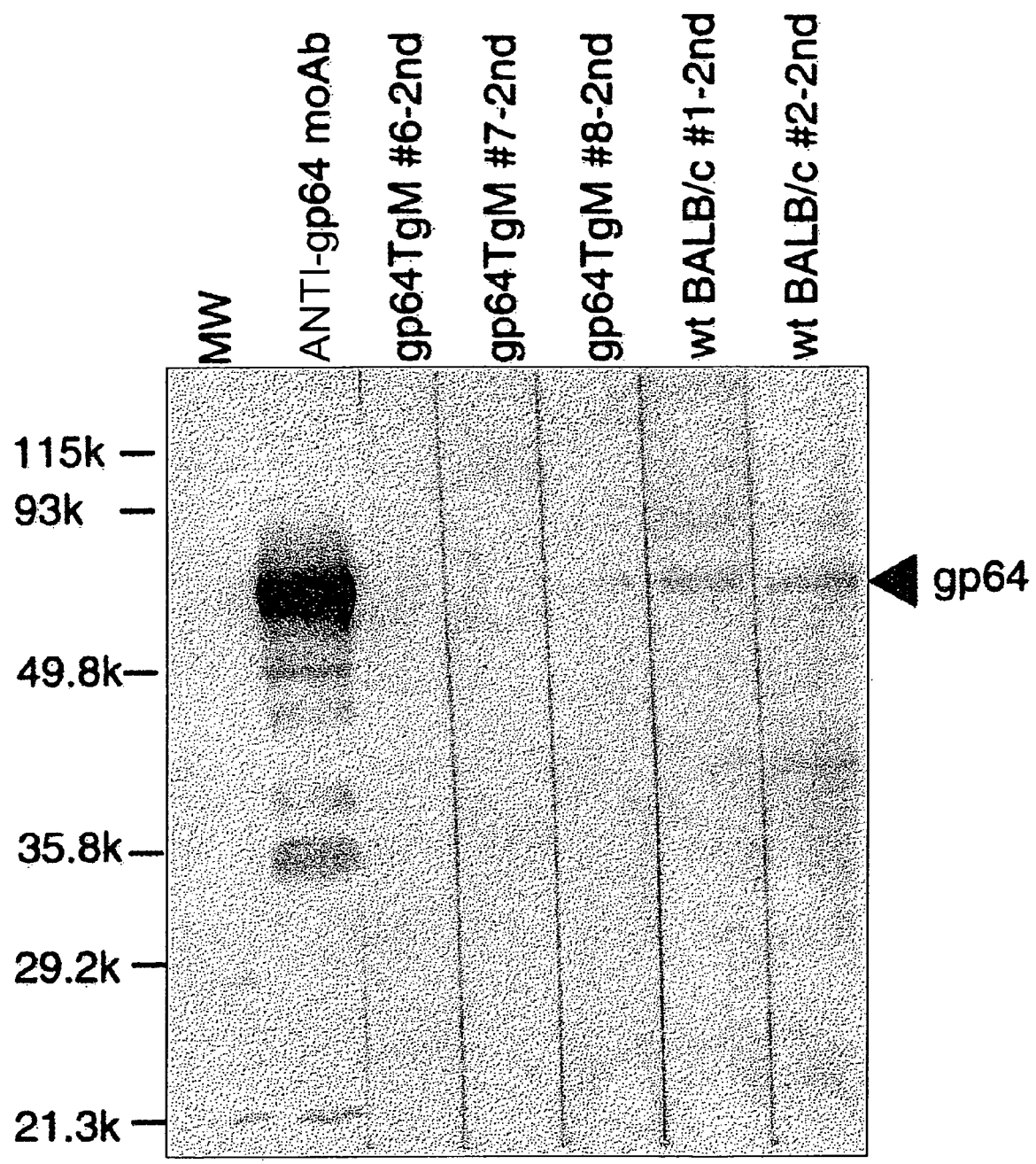
FIG. 7 is a photograph showing the results of Western blotting analysis using anti-mouse IgG. Gp64TgM and wtBALB/c represent transgenic and non-transgenic mice, respectively.

FIG. 6 shows the results. When stained with the Anti-Mouse IgG, a band corresponding to the gp64 protein was strongly stained for the lanes reacted with both of the two serum samples obtained from non-transgenic mice. On the other hand, though gp64 was detected in all three gp64 transgenic mice, staining was weak. These results indicate that the amount of anti-gp64 antibody produced by the transgenic mice is considerably less than that produced by non-transgenic mice. Although the Anti-Mouse IgM staining was weak for the two non-transgenic mice, it was very weak or not stained at all in the gp64 transgenic mice (FIG. 7).

EXAMPLE 9

Production of anti-PepT1 Antibodies by gp64 Tgm

Following procedures were used for the initial immunization. 200 µl PBS comprising 1 mg of PepT1-BV and 100 ng of pertussis toxin was subcutaneously injected into Tgm. For the second and subsequent immunizations, 0.5 mg of PepT1-BV suspension in PBS was subcutaneously injected.

Ba/F3 cells expressing PepT1 on the cell surface (hereinafter, referred to as Ba/F3-PepT1) and Ba/F3 cells expressing no PepT1 were washed twice with PBS, respectively. 100 µl of mouse serum sample that was 220 fold-diluted with PBS was added to $1 \times 10^6$ cells of each cell type, followed by reaction for 30 minutes on ice. After reaction, cells were washed once with 500 µl PBS and 100 µl of FITC-anti-mouse IgG 200 fold-diluted with PBS was added. This was allowed to react for 30 minutes on ice. After centrifugation, cells were suspended in 500 µl of PBS and analyzed by FACS. FIGS. 8 and 9 show the results of FACS analysis of a serum obtained from a mouse after the fifth immunization. In these figures, solid lines and dotted lines indicate Ba/F3 and Ba/F3-PepT1 cells, respectively.

From these results, the titer of antibody reacting specifically with Pep-T1 was confirmed to be increased in the serum of mice immunized with PepT1-BV.

INDUSTRIAL APPLICABILITY

This invention enables efficient production of antibodies against target antigens, using target antigens that comprise background antigens. The antibody-production methods of the present invention are useful in producing antibodies by using immunogens in which contamination by background antigens is inevitable.

For example, an exogenous gene expression system, known as the baculovirus expression system, is useful as a tool for obtaining recombinant proteins easily and in large quantities. In particular, when applied to membrane proteins, the baculovirus expression system is excellent in that the membrane proteins are obtainable with other viral envelope proteins in a state that maintains their structure. However, this expression system is also problematic in that, when using this expression product as the immunogen, gp64 acts as a background antigen and interferes with the acquisition of antibodies against a target antigen.

By using the antibody-production methods of the present invention, it is possible to efficiently suppress the adverse effect of background antigens on the proteins prepared by the baculovirus expression system. As a result, anti-membrane protein antibodies can be produced efficiently by using the membrane protein antigens, which can be obtained in large quantities using the baculovirus expression system, as target antigens.

Membrane proteins include many functionally important proteins such as receptors and cell adhesive proteins. Therefore, antibodies that recognize membrane proteins are expected to play an important role in functional analysis, localization analysis, quantification, diagnosis, or the development of therapeutic agents that regulate membrane protein activities.

Preparation of membrane proteins applicable as immunogens has been thought to be difficult. However, by the present invention, large quantities of membrane proteins produced by, for example, the baculovirus expression system, can be used as immunogens without removing background antigens. Consequently, many antibodies that recognize various membrane proteins and that have been considered to be difficult to produce can now obtained very efficiently.

The antibody-production methods of the present invention contribute to the functional analysis of membrane proteins and diagnosis using antibodies, and to the development of drugs based on the regulation of membrane protein activities.

All prior art documents cited in the present application are hereby incorporated by reference in their entirety.

The invention claimed is:

1. A method for producing an antibody against PepT1, wherein the method comprises the steps of: (a) immunizing a transgenic mouse with an immunogen comprising a budding baculovirus that expresses PepT1 or a fragment thereof or a fraction of the budding baculovirus comprising PepT1 or a fragment thereof, wherein the genome of the transgenic mouse comprises a gene encoding a baculovirus membrane protein gp64, and wherein the transgenic mouse expresses the baculovirus membrane protein gp64 and has immunotolerance to gp64; and (b) recovering an antibody recognizing PepT1 from the immunized transgenic mouse.

2. A method for producing an antibody against antigen, wherein the method comprises the steps of: (a) immunizing a transgenic mouse with an immunogen comprising a budding baculovirus that expresses the antigen or an epitope thereof or a fraction of the budding baculovirus comprising the antigen or an epitope thereof, wherein the genome of the transgenic mouse comprises a gene encoding a baculovirus membrane protein gp64, and wherein the transgenic mouse expresses the baculovirus membrane protein gp64 and has immunotolerance to gp64; and (b) recovering an antibody recognizing the antigen or epitope thereof from the immunized transgenic mouse.

* * * * *